(12) United States Patent
Zhang et al.

(10) Patent No.: US 8,735,409 B2
(45) Date of Patent: May 27, 2014

(54) QUINAZOLINE DERIVATIVES

(76) Inventors: Qiang Zhang, Somerset, NJ (US);
Hongwen Zhu, Bronx, NY (US)

(*) Notice: Subject to any disclaimer, the term of this patent is extended or adjusted under 35 U.S.C. 154(b) by 9 days.

(21) Appl. No.: 13/513,982

(22) PCT Filed: Dec. 21, 2010

(86) PCT No.: PCT/US2010/061567
§ 371 (c)(1),
(2), (4) Date: Jun. 5, 2012

(87) PCT Pub. No.: WO2011/084796
PCT Pub. Date: Jul. 14, 2011

(65) Prior Publication Data
US 2013/0035350 A1 Feb. 7, 2013

Related U.S. Application Data

(60) Provisional application No. 61/288,492, filed on Dec. 21, 2009.

(51) Int. Cl.
*A01N 43/54* (2006.01)
*A61K 31/519* (2006.01)
*C07D 239/72* (2006.01)
*C07D 401/00* (2006.01)

(52) U.S. Cl.
USPC .................. 514/266.2; 514/266.1; 544/283; 544/284

(58) Field of Classification Search
USPC .................. 514/266.1, 266.2; 544/283, 284
See application file for complete search history.

(56) References Cited

U.S. PATENT DOCUMENTS

| RE43,431 E | 5/2012 | Himmelsbach et al. |
|---|---|---|
| 2002/0173509 A1 | 11/2002 | Himmelsbach et al. |
| 2006/0100223 A1 | 5/2006 | Himmelsbach et al. |
| 2010/0010023 A1 | 1/2010 | Himmelsbach et al. |
| 2011/0046168 A1 | 2/2011 | Himmelsbach et al. |

FOREIGN PATENT DOCUMENTS

| WO | WO2008076949 A2 | 6/2008 |
|---|---|---|
| WO | WO2008033748 A3 | 12/2008 |
| WO | WO2008033749 A3 | 12/2008 |
| WO | WO2009094210 A1 | 7/2009 |

OTHER PUBLICATIONS

Pinedo et al (2001).*
McMahon et al (2001).*
Mishani et al., "Novel carbon-11 labeled 4-dimethylamino-but-2-enoic acid [4-(phenylamino)-quinazoline-6-yl)amides: potential PET bioprobes for molecular imaging of EGFR-positive tumors." Nuclear Medicine and Biology 31, pp. 469-476, May 2004.
O'Driscoll, "Heavyweight drugs: swapping selected hydrogen atoms for deuterium could be a fast route to making safer, longer lasting drugs." Entrepreneur, pp. 1-4, Mar. 9, 2009.
Zhong et al., "Induced-fit docking studies of the active and inactive states of protein tyrosine kinases", Journal of Molecular Graphics and Modelling 28, pp. 336-346, Aug. 31, 2009.
PCT International Search Report mailed Oct. 31, 2011 issued in corresponding International Application No. PCT/US2010/061567.

* cited by examiner

*Primary Examiner* — Paul V. Ward
(74) *Attorney, Agent, or Firm* — Fish & Richardson P.C.

(57) ABSTRACT

This disclosure concerns novel quinazoline compounds of Formula (I) as defined in the specification and compositions comprising such novel compounds. These compounds are useful anticancer agents, especially in inhibiting the function of the EGF receptor tyrosine kinases, HER1 tyrosine kinase, and HER2 tyrosine kinase. Thus, the disclosure also concerns a method of treating hyperproliferative diseases or conditions, such as various cancers and benign prostate hyperplasia (BPH), by use of these novel compounds or a composition comprising such novel compounds.

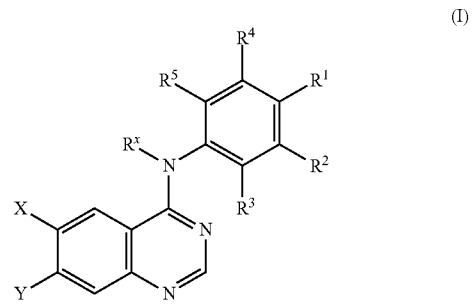

17 Claims, No Drawings

QUINAZOLINE DERIVATIVES

CROSS-REFERENCE TO RELATED APPLICATIONS

This application is the National Stage of International Application No. PCT/US2010/061567, filed on Dec. 21, 2010, which claims priority under 35 U.S.C. §119(e) to U.S. Provisional Patent Application Serial No. 61/288,492, filed on Dec. 21, 2009, which is hereby incorporated by reference in its entirety.

FIELD OF THE INVENTION

The present invention relates to novel 4-phenylamino-quinazoline derivatives, and the stereoisomers, pharmaceutically acceptable salts or solvates, and prodrugs thereof useful for the treatment of hyperproliferative diseases, such as various cancers and benign prostate hyperplasia (BPH).

BACKGROUND OF THE INVENTION

A cell may become cancerous through transformation of a portion of its DNA into an oncogene, i.e., a gene that on activation leads to the formation of malignant tumor cells. Many oncogenes encode proteins that are aberrant tyrosine kinases capable of causing cell transformations. Alternatively, the overexpression of a normal proto-oncogenic tyrosine kinase may result in proliferative disorders, sometimes of a malignant phenotype.

Receptor tyrosine kinases are large enzymes spanning the cell membrane and having an extracellular binding domain for growth factors (such as epidermal growth factor), a transmembrane domain, and an intracellular portion that functions as a kinase to phosphorylate specific tyrosine residues in proteins, hence to influence cell proliferation. Such tyrosine kinases are often aberrantly expressed in common human cancers such as breast cancer, gastrointestinal cancers (such as colon, rectal and stomach cancers), leukemia, and ovarian, bronchial or pancreatic cancer. It has also been shown that epidermal growth factor receptor (EGFR), which possesses tyrosine kinase activity, is mutated and/or overexpressed in many human cancers, such as brain, lung, squamous cell, bladder, gastric, breast, head and neck, oesophasgeal, gynecological, and thyroid tumors.

Accordingly, it has been recognized that inhibitors of receptor tyrosine kinases are useful as selective inhibitors to the growth of mammalian cancer cells. For example, erbstatin, a tyrosine kinase inhibitor selectively attenuates the growth in athymic nude mice of a transplanted human mammary carcinoma that expresses epidermal growth factor receptor tyrosine kinase (EGFR), but it is not effective on inhibiting the growth of another carcinoma that does not express the EGF receptor.

Various compounds, such as styrene and quinazoline derivatives, have been reported to possess anti-cancer properties, as a result of their tyrosine kinase inhibitory properties, (see, e.g., EP 0 566 226 A2, EP 0 602 851 A1, EP 0 635 507 A1, EP 0 635 498 A1 and EP 0 520 722 A1) (U.S. Pat. No. 5,747,498).

EGF type receptor tyrosine kinases are also implicated in various non-malignant proliferative disorders, and therefore inhibitors of EGF type receptor tyrosine kinases have been reported to be useful for the treatment of non-malignant diseases of excessive cellular proliferation, such as psoriasis (where TGFα is believed to be the most important growth factor), benign prostatic hypertrophy (BPH), atherosclerosis, and restenosis.

Quinazoline derivatives, including the ones bearing an anilino substituent at the 4-position, an alkoxy substituent at the 7-position, and an alkoxy substituent at the 6-position, have been disclosed to possess anti-cancer activities (see, e.g., U.S. Pat. No. 5,770,599, U.S. Pat. No. 5,747,498, EP 1,110,953, EP 8 17,775, U.S. Pat. No. 6,476,040, and Jänne, P. A. et al., Nat. Rev. Drug Discov., 2009, 8(9):709-23). In particular, Erlotinib, also known as [6,7-bis-(2-methoxyethoxy)-quinazolin-4-yl]-(3-ethynylphenyl)-amine or N-(3-ethynylphenyl)-6,7-bis(2-methoxyethoxy)quinazolin-4-amine, is an inhibitor of EGF receptor tyrosine kinases approved in the United States and Europe for the treatment of locally advanced or metastatic non-small cell lung cancer (NSCLC). Erlotinib is particularly effective for the patients who have failed in at least one prior chemotherapy regimen. A combination therapy of Erlotinib with a nucleoside analog, gemcitabine, has also been approved in the United States for the treatment of metastatic pancreatic cancer. Erlotinib, alone or in combination with other agents, is also being investigated in the clinical trials for the treatment of a variety of cancers, including, but not limited to lung cancer, pancreatic cancer, astrocytoma, renal cancer, head and neck cancer, breast cancer, bladder cancer, ovarian cancer, colorectal cancer, prostate cancer, cervical cancer, thymoma cancer, liver cancer and gastric cancer. Erlotinib has also been thought to be useful in the treatment of benign prostate hyperplasia (BPH).

Tykerb (Lapatinib), another 4-(substituted phenylamino) quinazoline analog, is used as a second-generation treatment for solid tumor. As a dual-HER1/HER2 tyrosine kinase inhibitor, it is believed to be more effective for the patients who are naturally HER1 resistant or have acquired such resistance. Tovok (BIBW 2992), another 4-(substituted phenylamino) quinazoline analog, is also an anti-cancer agent, which has entered Phase III clinical trials for non-small cell lung carcinoma and phase II trials for breast, prostate, and head and neck cancers, as well as glioma. It has a chemically reactive group to irreversibly modify the target residues to increase the efficacy for the treatment of cancer patients. As another example of irreversible anti-cancer agents, CUDC-101, a multiple inhibitor for EGFR, HER2 and histone deacetylase is also in clinical trials for different kinds of cancers.

Although the above examples have shown that the 4-(substituted phenylamino) quinazoline represents a privileged core structure, based on which useful anticancer agents, such as Erlotinib, Gefitinib and Lapatinib, have been developed (see, e.g., Zhang, J. et al., Nat. Rev. Cancer, 2009, 9(1):28-39), extensive research is still being conducted to discover novel therapeutic agents containing the same core structure. There is a continuing need for the development of new anti-cancer agents that are more effective, yet less toxic, for the treatment of the aforementioned diseases and conditions.

SUMMARY OF THE INVENTION

This invention fulfills the forgoing needs by providing novel 4-(substituted phenylamino) quinazoline derivatives as useful inhibitors to various receptor tyrosine kinases, and thus anticancer agents. These novel compounds are advantageous over the existing anti-cancer agents, because they possess better stability while potentially maintaining or improving the therapeutic potency.

In one aspect the present disclosure provides a compound of Formula (I):

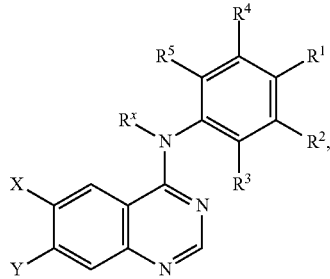

or a stereoisomer, a prodrug, or a pharmaceutically acceptable salt or solvate thereof, wherein:

$R^1$, $R^2$, $R^3$, $R^4$, and $R^5$ are each independently selected from hydrogen, deuterium, alkyl, alkenyl, alkynyl, cycloalkyl, aryl, heteroaryl, heterocyclyl, halogen, cyano, -L-$R^6$, —$OR^7$, —$C(O)OR^8$, —$OC(O)R^9$, —$C(O)R^{10}$, —$SR^{11}$, —$S(O)_2R^{12}$, —$S(O)R^{12}$, —$NR^aR^b$, and —$NHC(O)R^{13}$, wherein said alkyl, alkenyl, alkynyl, cycloalkyl, aryl, heteroaryl, and heterocyclyl each may optionally comprise one or more deuterium atoms;

X and Y are each independently selected from the group consisting of hydrogen, deuterium, alkyl, alkenyl, alkynyl, cycloalkyl, aryl, heteroaryl, heterocyclyl, halogen, cyano, —$C(O)OR^8$, —$OC(O)R^9$, —$C(O)R^{10}$, —$SR^{11}$, —$S(O)_2R^{12}$, —$S(O)R^{12}$, —$NR^aR^b$, —$OR^{14}$, —O-$L^1$-$R^{15}$, —$N(R^x)C(O)R^{16}$, —O-$(L^2$-O$)_n$—$R^{18}$,

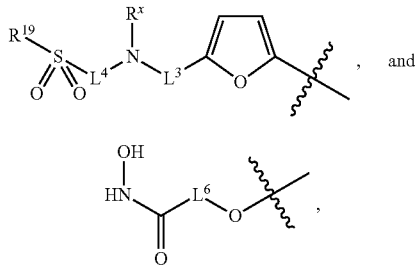

wherein said alkyl, alkenyl, alkynyl, cycloalkyl, aryl, heteroaryl, and heterocyclyl each may optionally comprise one or more deuterium atoms;

n is 0, 1, or 2;

L is $C_1$-$C_4$ alkylene optionally comprising one or more deuterium atoms;

$L^1$ is $C_1$-$C_4$ alkylene optionally comprising one or more deuterium atoms;

$L^2$, at each occurrence, is independently ethylene optionally comprising one to four deuterium atoms;

$L^3$ is methylene or ethylene optionally comprising one or more deuterium atoms;

$L^4$ is $C_1$-$C_3$ alkylene optionally comprising one or more deuterium atoms $L^6$ is $C_1$-$C_{18}$ alkylene optionally comprising one or more deuterium atoms;

$R^x$, at each occurrence, is independently hydrogen or deuterium;

$R^6$ is selected from hydrogen, deuterium, $C_1$-$C_4$ alkyl, aryl, heteroaryl, cycloalkyl, carbocyclyl, heterocyclyl, —$SR^{11}$, and —$OR^7$, wherein said alkyl, aryl, heteroaryl, cycloalkyl, carbocyclyl, and heterocyclyl each may optionally comprise one or more deuterium atoms;

$R^7$ is hydrogen, deuterium, $C_1$-$C_6$ alkyl, aryl, heteroaryl, cycloalkyl, carbocyclyl, heterocyclyl, or -$L^5$-$R^{20}$, wherein said alkyl, aryl, heteroaryl, cycloalkyl, carbocyclyl, and heterocyclyl each may optionally comprise one or more deuterium atoms;

$R^8$ is hydrogen, deuterium, $C_1$-$C_6$ alkyl, or benzyl, wherein said alkyl and benzyl each may optionally comprise one or more deuterium atoms;

$R^9$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{10}$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{11}$ is hydrogen, deuterium, $C_1$-$C_6$ alkyl, cycloalkyl, aryl, heteroaryl, or heterocyclyl, wherein said alkyl, cycloalkyl, aryl, heteroaryl, and heterocyclyl each may optionally comprise one or more deuterium atoms;

$R^{12}$ is $C_1$-$C_6$ alkyl, $C_3$-$C_6$ cycloalkyl, aryl, heteroaryl, or $NR^cR^d$, wherein said alkyl, cycloalkyl, aryl, and heteroaryl each may optionally comprise one or more deuterium atoms;

$R^{13}$ is $C_3$-$C_6$ cycloalkyl optionally substituted by one or more substituents independently selected from halogen, $C_1$-$C_6$ alkyl, $C_1$-$C_6$ alkoxy, oxo, or —$C(O)NR^cR^d$ and optionally comprising one or more deuterium atoms;

$R^{14}$ is selected from hydrogen, deuterium, $C_1$-$C_6$ allyl, carbocyclyl, heterocyclyl, and -$L^2$-O—$R^{18}$, wherein said alkyl, carbocyclyl, and heterocyclyl each may optionally comprise one or more deuterium atoms;

$R^{15}$ is selected from hydrogen, deuterium, $C_1$-$C_6$ alkyl, carbocyclyl, heterocyclyl, and —$OR^{21}$, wherein said alkyl, carbocyclyl, and heterocyclyl each may optionally comprise one or more deuterium atoms;

$R^{16}$ is selected from

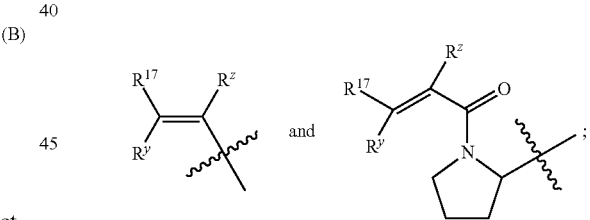

$R^y$ and $R^z$ are each independently hydrogen or deuterium;

$R^{17}$ is selected from hydrogen, deuterium, -L-$R^6$, -L-$OR^7$, -L-$SR^{11}$, and -L-$NR^eR^f$;

$R^{18}$ is -$L^5$-O—$R^{22}$ or $C_1$-$C_6$ alkyl optionally comprising one or more deuterium atoms;

$L^5$ is methylene or ethylene, each optionally comprising one or more deuterium atoms;

$R^{19}$ is $C_1$-$C_6$ alkyl optionally comprising one or more deuterium atoms;

$R^{20}$ is aryl or heteroaryl, each optionally comprising one or more deuterium atoms;

$R^{21}$ is $C_1$-$C_6$ alkyl optionally comprising one or more deuterium atoms;

$R^{22}$ is selected from $C_1$-$C_6$ alkyl, $C_3$-$C_6$ cycloalkyl, heterocyclyl, aryl, and heteroaryl, each optionally substituted by $C_1$-$C_6$ alkyl, wherein said alkyl, cycloalkyl, heterocyclyl, aryl, and heteroaryl each may optionally comprise one or more deuterium atoms;

$R^a$ and $R^b$ are independently selected from hydrogen, deuterium, alkyl, alkenyl, alkynyl, aryl, heteroaryl, and benzyl, wherein said alkyl, alkenyl, alkynyl, aryl, heteroaryl, and benzyl each may optionally comprise one or more deuterium atoms;

$R^c$ and $R^d$ are each independently hydrogen, deuterium, $C_1$-$C_6$ alkyl, benzyl, or aryl wherein said alkyl, aryl, and benzyl each may optionally comprise one or more deuterium atoms; and $R^e$ and $R^f$ are each independently hydrogen, deuterium, or $C_1$-$C_4$ alkyl optionally comprising one or more deuterium atoms;

wherein any said aryl, heteroaryl, and benzyl each may optionally be substituted with one to five substituents independently selected from $C_1$-$C_6$ alkyl, $C_1$-$C_4$ haloalkyl, $C_1$-$C_6$ alkoxy, $C_1$-$C_4$ haloalkoxy, halogen, hydroxyl, cyano, and nitro;

wherein any said carbocyclyl, cycloalkyl, or heterocyclyl may optionally be substituted with one or more substituents independently selected from $C_1$-$C_6$ alkyl, $C_1$-$C_4$ haloalkyl, $C_1$-$C_6$ alkoxy, halogen, hydroxyl, and oxo;

wherein each said alkyl, haloalkyl, alkoxy, haloalkoxy, and hydroxyl each may optionally comprise one or more deuterium atoms; and wherein at least one of $R^1$, $R^2$, $R^3$, $R^4$, $R^5$, $R^x$, X, or Y comprises one or more deuterium atoms, provided that:

(a) when X and Y are each independently —O-$L^2$-O—$R^{18}$, and $R^1$ is selected from hydrogen, deuterium, halogen, —OH, —OCD$_3$, and —OCH$_3$, then neither $R^2$ nor $R^4$ is hydrogen, deuterium, halogen, CF$_3$, —C≡CH or —C≡CD;

(b) when X is —O-$L^1$-$R^{15}$, Y is —OR$^{14}$, $R^{15}$ is 4-morpholinyl or deuterated morpholinyl, and either one of $R^2$ or $R^4$ is chloro, then $R^{14}$ is not hydrogen, methyl, or deuterated methyl;

(c) when X is —OR$^{14}$, Y is —O-$L^1$-$R^{15}$, $R^{15}$ is a 4-piperidinyl or deuterated 4-piperidinyl group, $L^1$ is methylene or deuterated methylene, $R^1$ is bromo, and either $R^3$ or $R^5$ is fluoro, then $R^{14}$ is not methyl or deuterated methyl; and (d) when X is a group of formula (A), Y is hydrogen or deuterium, $R^1$ is —OR$^7$, and $R^{19}$ is methyl or deuterated methyl, then $R^7$ is not 3-fluorobenzyl or deuterated 3-fluorobenzyl.

The compounds of the present disclosure can be effective to inhibit the function of various protein kinases and thus useful for the treatment of hyperproliferative diseases or disorders. In particular, the compounds of the present disclosure can be effective to inhibit the epidermal growth factor receptor (EGFR) tyrosine kinase, HER1 tyrosine kinase, and HER2 tyrosine kinase and histone deacetylase. Therefore, this invention also encompasses: (1) compositions comprising a compound of Formula (I), or a stereoisomer, a pharmaceutically acceptable salt, or a solvate thereof, and a pharmaceutically acceptable carrier; (2) a method of treating an antihyperproliferative disease or condition in a patient, comprising administering to the patient a therapeutically effective amount of a compound of Formula (I), or a pharmaceutically acceptable salt or solvate thereof; and (3) use of a compound of Formula (I) for manufacture of a medicament for treatment of hyperproliferative diseases or disorders.

DETAILED DESCRIPTION OF THE INVENTION

In a first aspect the present disclosure provides compounds of Formula (I):

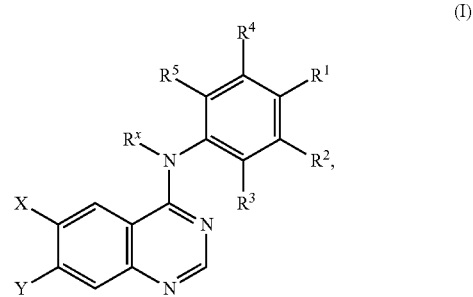

or a stereoisomer, a prodrug, or a pharmaceutically acceptable salt or solvate thereof, wherein:

$R^1$, $R^2$, $R^3$, $R^4$, and $R^5$ are each independently selected from hydrogen, deuterium, alkyl, alkenyl, alkynyl, cycloalkyl, aryl, heteroaryl, heterocyclyl, halogen, cyano, -L-$R^6$, —OR$^7$, —C(O)OR$^8$, —OC(O)R$^9$, —C(O)R$^{10}$, —SR$^{11}$, —S(O)$_2$R$^{12}$, —S(O)R$^{12}$, —NR$^a$R$^b$, and —NHC(O)R$^{13}$, wherein said alkyl, alkenyl, alkynyl, cycloalkyl, aryl, heteroaryl, and heterocyclyl each may optionally comprise one or more deuterium atoms; X and Y are each independently selected from the group consisting of hydrogen, deuterium, alkyl, alkenyl, alkynyl, cycloalkyl, aryl, heteroaryl, heterocyclyl, halogen, cyano, —C(O)OR$^8$, —OC(O)R$^9$, —C(O)R$^{10}$, —SR$^{11}$, —S(O)$_2$R$^{12}$, —S(O)R$^{12}$, —NR$^a$R$^b$, —OR$^{14}$, —O-$L^1$-R$^{15}$, —N(R$^x$)C(O)R$^{16}$, —O-(L$^2$-O)$_n$—R$^{18}$,

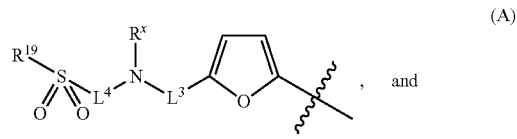

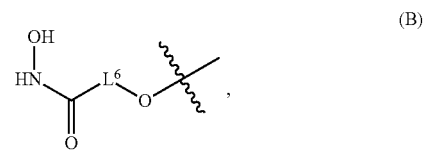

wherein said alkyl, alkenyl, alkynyl, cycloalkyl, aryl, heteroaryl, and heterocyclyl each may optionally comprise one or more deuterium atoms;

n is 0, 1, or 2;

L is $C_1$-$C_4$ alkylene optionally comprising one or more deuterium atoms;

$L^1$ is $C_1$-$C_4$ alkylene optionally comprising one or more deuterium atoms;

$L^2$, at each occurrence, is independently ethylene optionally comprising one to four deuterium atoms;

$L^3$ is methylene or ethylene optionally comprising one or more deuterium atoms;

$L^4$ is $C_1$-$C_3$ alkylene optionally comprising one or more deuterium atoms;

$L^6$ is $C_1$-$C_{18}$ alkylene optionally comprising one or more deuterium atoms;

$R^x$, at each occurrence, is independently hydrogen or deuterium;

$R^6$ is selected from hydrogen, deuterium, $C_1$-$C_4$ alkyl, aryl, heteroaryl, cycloalkyl, carbocyclyl, heterocyclyl, —$SR^{11}$, and —$OR^7$, wherein said alkyl, aryl, heteroaryl, cycloalkyl, carbocyclyl, and heterocyclyl each may optionally comprise one or more deuterium atoms;

$R^7$ is hydrogen, deuterium, $C_1$-$C_6$ alkyl, aryl, heteroaryl, cycloalkyl, carbocyclyl, heterocyclyl, or -$L^5$-$R^{20}$, wherein said alkyl, aryl, heteroaryl, cycloalkyl, carbocyclyl, and heterocyclyl each may optionally comprise one or more deuterium atoms;

$R^8$ is hydrogen, deuterium, $C_1$-$C_6$ alkyl, or benzyl, wherein said alkyl and benzyl each may optionally comprise one or more deuterium atoms;

$R^9$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{10}$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{11}$ is hydrogen, deuterium, $C_1$-$C_6$ alkyl, cycloalkyl, aryl, heteroaryl, or heterocyclyl, wherein said alkyl, cycloalkyl, aryl, heteroaryl, and heterocyclyl each may optionally comprise one or more deuterium atoms;

$R^{12}$ is $C_1$-$C_6$ alkyl, $C_3$-$C_6$ cycloalkyl, aryl, heteroaryl, or $NR^cR^d$, wherein said alkyl, cycloalkyl, aryl, and heteroaryl each may optionally comprise one or more deuterium atoms;

$R^{13}$ is $C_3$-$C_6$ cycloalkyl optionally substituted by one or more substituents independently selected from halogen, $C_1$-$C_6$ alkyl, $C_1$-$C_6$ alkoxy, oxo, or —$C(O)NR^cR^d$ and optionally comprising one or more deuterium atoms;

$R^{14}$ is selected from hydrogen, deuterium, $C_1$-$C_6$ alkyl, carbocyclyl, heterocyclyl, and -$L^2$-O—$R^{18}$, wherein said alkyl, carbocyclyl, and heterocyclyl each may optionally comprise one or more deuterium atoms;

$R^{15}$ is selected from hydrogen, deuterium, $C_1$-$C_6$ alkyl, carbocyclyl, heterocyclyl, and —$OR^{21}$, wherein said alkyl, carbocyclyl, and heterocyclyl each may optionally comprise one or more deuterium atoms;

$R^{16}$ is selected from

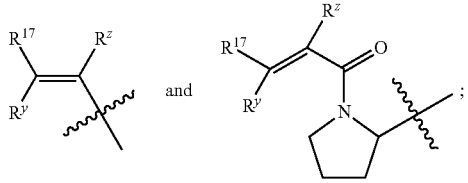

$R^y$ and $R^z$ are each independently hydrogen or detuerium;

$R^{17}$ is selected from hydrogen, deuterium, -L-$R^6$, -L-$OR^7$, -L-$SR^{11}$, and -L-$NR^eR^f$;

$R^{18}$ is -$L^5$-O—$R^{22}$ or $C_1$-$C_6$ alkyl optionally comprising one or more deuterium atoms;

$L^5$ is methylene or ethylene, each optionally comprising one or more deuterium atoms;

$R^{19}$ is $C_1$-$C_6$ alkyl optionally comprising one or more deuterium atoms;

$R^{20}$ is aryl or heteroaryl, each optionally comprising one or more deuterium atoms;

$R^{21}$ is $C_1$-$C_6$ alkyl optionally comprising one or more deuterium atoms;

$R^{22}$ is selected from $C_1$-$C_6$ alkyl, $C_3$-$C_6$ cycloalkyl, heterocyclyl, aryl, and heteroaryl, each optionally substituted by $C_1$-$C_6$ alkyl, wherein said alkyl, cycloalkyl, heterocyclyl, aryl, and heteroaryl each may optionally comprise one or more deuterium atoms;

$R^a$ and $R^b$ are independently selected from hydrogen, deuterium, alkyl, alkenyl, alkynyl, aryl, heteroaryl, and benzyl, wherein said alkyl, alkenyl, alkynyl, aryl, heteroaryl, and benzyl each may optionally comprise one or more deuterium atoms;

$R^c$ and $R^d$ are each independently hydrogen, deuterium, $C_1$-$C_6$ alkyl, benzyl, or aryl wherein said alkyl, aryl, and benzyl each may optionally comprise one or more deuterium atoms; and $R^e$ and $R^f$ are each independently hydrogen, deuterium, or $C_1$-$C_4$ alkyl optionally comprising one or more deuterium atoms;

wherein any said aryl, heteroaryl, and benzyl each may optionally be substituted with one to five substituents independently selected from $C_1$-$C_6$ alkyl, $C_1$-$C_4$ haloalkyl, $C_1$-$C_6$ alkoxy, $C_1$-$C_4$ haloalkoxy, halogen, hydroxyl, cyano, and nitro;

wherein any said carbocyclyl, cycloalkyl, or heterocyclyl may optionally be substituted with one or more substituents independently selected from $C_1$-$C_6$ alkyl, $C_1$-$C_4$ haloalkyl, $C_1$-$C_6$ alkoxy, halogen, hydroxyl, and oxo;

wherein each said alkyl, haloalkyl, alkoxy, haloalkoxy, and hydroxyl each may optionally comprise one or more deuterium atoms; and wherein at least one of $R^1$, $R^2$, $R^3$, $R^4$, $R^5$, $R^x$, X, or Y comprises one or more deuterium atoms, provided that:

(a) when X and Y are each independently —O-$L^2$-O—$R^{18}$, and $R^1$ is selected from hydrogen, deuterium, halogen, —OH, —$OCD_3$, and —$OCH_3$, then neither $R^2$ nor $R^4$ is hydrogen, deuterium, halogen, $CF_3$, —C≡CH, or —C≡CD;

(b) when X is —O-$L^1$-$R^{15}$, Y is —$OR^{14}$, $R^{15}$ is 4-morpholinyl or deuterated morpholinyl, and either one of $R^2$ or $R^4$ is chloro, then $R^{14}$ is not hydrogen, methyl, or deuterated methyl;

(c) when X is —$OR^{14}$, Y is —O-$L^1$-$R^{15}$, $R^{15}$ is a 4-piperidinyl or deuterated 4-piperidinyl group, $L^1$ is methylene or deuterated methylene, $R^1$ is bromo, and either $R^3$ or $R^5$ is fluoro, then $R^{14}$ is not methyl or deuterated methyl; and (d) when X is a group of formula (A), Y is hydrogen or deuterium, $R^1$ is —$OR^7$, and $R^{19}$ is methyl or deuterated methyl, then $R^7$ is not 3-fluorobenzyl or deuterated 3-fluorobenzyl.

In one embodiment of the first aspect, the present disclosure provides a compound of Formula (I), or a stereoisomer, a prodrug, or a pharmaceutically acceptable salt or solvate thereof, wherein:

$R^1$ is selected from hydrogen, deuterium, halogen, —$OR^7$, and —$NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^7$ is hydrogen, deuterium, $C_1$-$C_4$ alkyl, aryl, heteroaryl, or -$L^5$-$R^{20}$, wherein said alkyl, aryl, and heteroaryl may each optionally comprise one or more deuterium atoms;

$R^{13}$ is $C_3$-$C_6$ cyclopropyl optionally substituted by —C(O)$NR^cR^d$ and optionally comprising one or more deuterium atoms;

$R^{20}$ is aryl or heteroaryl, each optionally comprising one or more deuterium atoms;

X and Y are each independently selected from hydrogen, deuterium, —OR$^{14}$, —O-L$^1$-R$^{15}$, —NR$^a$R$^b$, —N(R$^x$)C(O)R$^{16}$, —O-(L$^2$-O)$_n$—R$^{18}$,

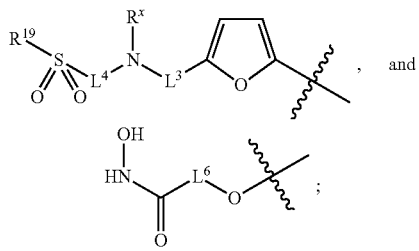

, and

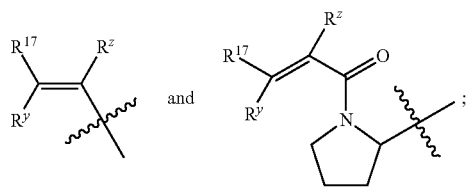

;

n is 0 or 1;

R$^{14}$ is selected from H, deuterium, C$_1$-C$_6$ alkyl, carbocyclyl, heterocyclyl, and -L$^2$-O—R$^{18}$, wherein each said alkyl, carbocyclyl, and heterocyclyl may optionally comprise one or more deuterium atoms;

R$^{15}$ is selected from hydrogen, deuterium, C$_1$-C$_4$ alkyl, carbocyclyl, heterocycyl, and —OR$^{21}$, wherein said alkyl, carbocyclyl, and heterocyclyl each may optionally comprise one or more deuterium atoms;

R$^{16}$ is selected from

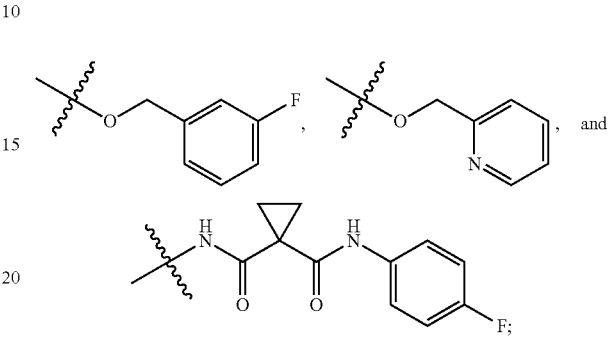

R$^y$ and R$^z$ are each independently hydrogen or detuerium;
R$^{17}$ is selected from hydrogen, deuterium, and -L-NR$^e$R$^f$;
R$^{18}$ is -L$^5$-O—R$^{22}$ or C$_1$-C$_6$ alkyl optionally comprising one or more deuterium atoms;
L is methylene or ethylene, each optionally comprising one or more deuterium atoms;
L$^1$ is C$_1$-C$_3$ alkylene optionally comprising one or more deuterium atoms;
L$^2$, at each occurrence, is independently ethylene optionally comprising one to four deuterium atoms;
L$^3$ is methylene optionally comprising one or two deuterium atoms;
L$^4$ is ethylene optionally comprising one to four deuterium atoms;
L$^5$, at each occurrence, is independently methylene or ethylene, each optionally comprising one or more deuterium atoms;
L$^6$ is C$_1$-C$_{18}$ alkylene optionally compromising one or more deuterium atoms;
R$^{19}$ is C$_1$-C$_6$ alkyl optionally comprising one or more deuterium atoms;
R$^{20}$ is aryl or heteroaryl, each optionally comprising one or more deuterium atoms;
R$^{21}$ is C$_1$-C$_6$ alkyl optionally comprising one or more deuterium atoms;
R$^{22}$ is selected from C$_1$-C$_6$ alkyl, C$_3$-C$_6$ cycloalkyl, heterocyclyl, aryl, and heteroaryl, each optionally comprising one or more deuterium atoms; and
R$^a$ and R$^b$ are independently selected from hydrogen, deuterium, C$_{1-6}$ alkyl, C$_{2-6}$ alkenyl, C$_{2-6}$ alkynyl, aryl, heteroaryl, and benzyl, wherein said alkyl, alkenyl, alkynyl, aryl, heteroaryl, and benzyl each may optionally comprise one or more deuterium atoms.

In another embodiment of the first aspect, the present disclosure provides a compound of Formula (I), or a stereoisomer, a prodrug, or a pharmaceutically acceptable salt or solvate thereof, wherein:

R$^1$ is selected from hydrogen, deuterium, F, Cl,

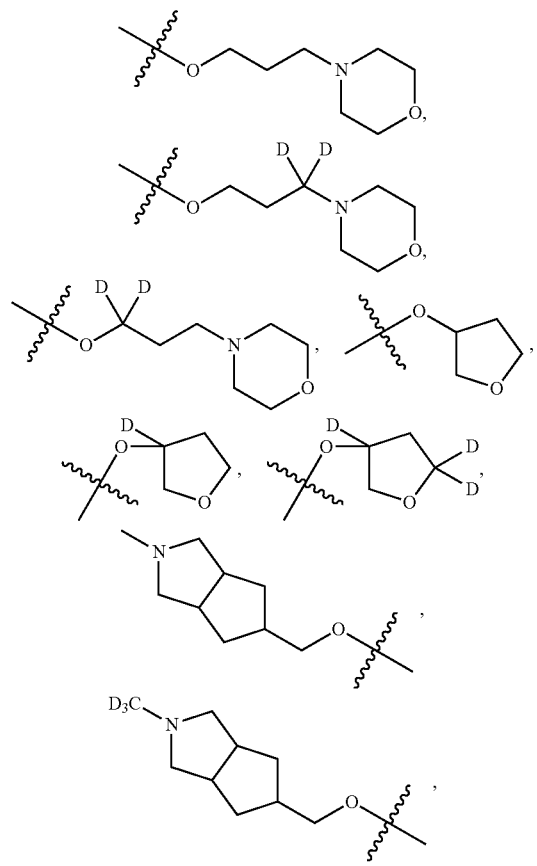

R$^2$ and R$^4$ are each independently selected from hydrogen, deuterium, F, Cl, —C≡CH, and —C≡CD;

R$^3$ and R$^5$ are each independently selected from hydrogen, deuterium, and F;

X is selected from —OCH$_2$CH$_2$OCH$_3$, —OCH$_2$CD$_2$OCH$_3$, —OCH$_2$CH$_2$OCD$_3$, —OCH$_2$CH$_2$OCD$_2$CH$_3$,

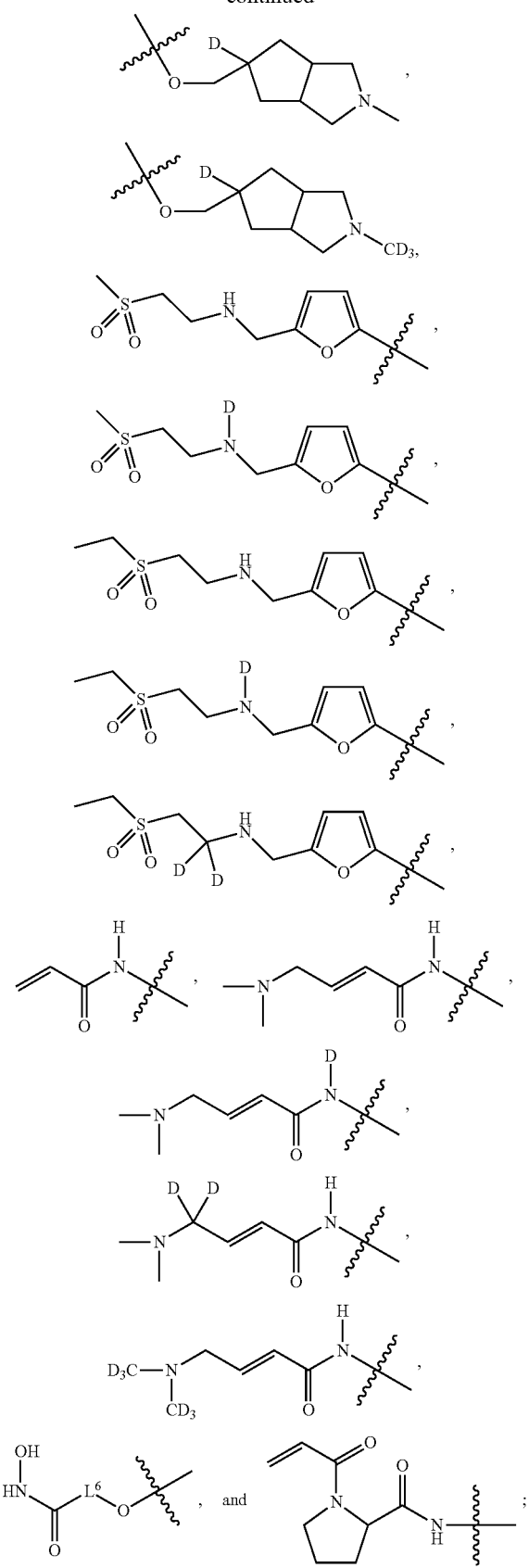

and

Y is selected from hydrogen, deuterium, —OCH$_3$, —OCD$_3$, —OCH$_2$CH$_3$, —OCD$_2$CH$_3$, —OCD$_2$CD$_3$, —OCH$_2$CH$_2$OCH$_3$, —OCH$_2$CD$_2$OCH$_3$, —OCH$_2$CH$_2$OCD$_3$, —OCH$_2$CH$_2$OCD$_2$CH$_3$,

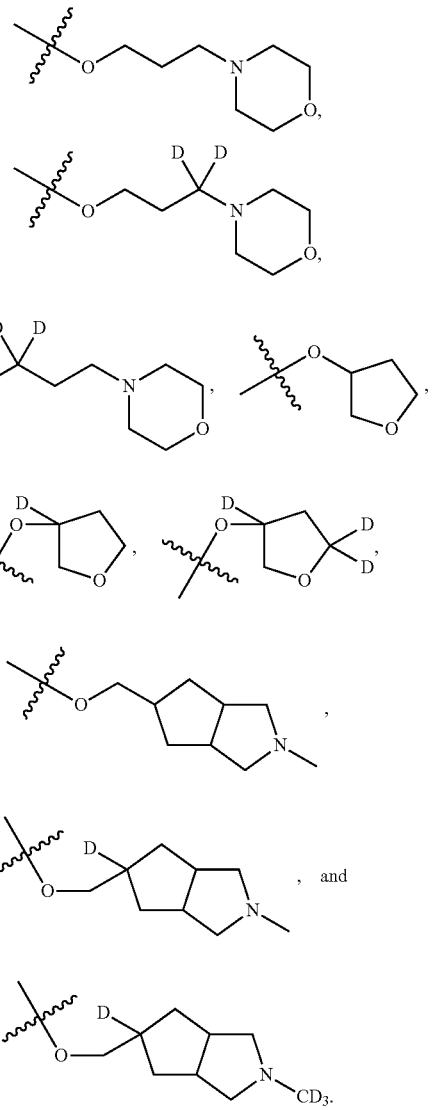

In another embodiment of the first aspect, the present disclosure provides a compound of Formula (I), or a stereoisomer, a prodrug, or a pharmaceutically acceptable salt or solvate thereof, wherein X and Y are each independently —O-(L$^2$-O)$_n$—R$^{18}$, wherein:

n is 1 or 2;

R$^{18}$ is methyl or ethyl optionally comprising one or more deuterium atoms; and L$^2$, at each occurrence, is independently ethylene optionally comprising one to four deuterium atoms.

In another embodiment of the first aspect, the present disclosure provides a compound of Formula (I), wherein X and Y are independently —O-L$^2$-O—R$^{18}$, further characterized by formula (Ia):

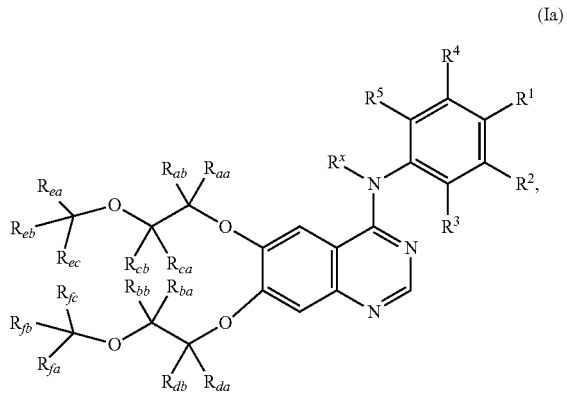

(Ia)

or a stereoisomer, a prodrug, or a pharmaceutically acceptable salt or solvate thereof, wherein:

$R^x$, at each occurrence, is independently hydrogen or deuterium;

$R^1$, $R^2$, $R^3$, $R^4$, and $R^5$ are each independently selected from hydrogen, deuterium, alkyl, alkenyl, alkynyl, cycloalkyl, aryl, heteroaryl, heterocyclyl, halogen, cyano, -L-$R^6$, —$OR^7$, —$C(O)OR^8$, —$OC(O)R^9$, —$C(O)R^{10}$, —$SR^{11}$, —$S(O)_2R^{12}$, —$S(O)R^{12}$, —$NR^aR^b$, and —$NHC(O)R^{13}$, wherein said alkyl, alkenyl, alkynyl, cycloalkyl, aryl, heteroaryl, and heterocyclyl each may optionally comprise one or more deuterium atoms;

$R^6$ is selected from hydrogen, deuterium, $C_1$-$C_4$ alkyl, aryl, heteroaryl, cycloalkyl, carbocyclyl, heterocyclyl, —$SR^{11}$, and —$OR^7$, wherein said alkyl, aryl, heteroaryl, cycloalkyl, carbocyclyl, and heterocyclyl each may optionally comprise one or more deuterium atoms;

$R^7$ is hydrogen, deuterium, $C_1$-$C_6$ alkyl, aryl, heteroaryl, cycloalkyl, carbocyclyl, heterocyclyl, or -$L^5$-$R^{20}$, wherein said alkyl, aryl, heteroaryl, cycloalkyl, carbocyclyl, and heterocyclyl each may optionally comprise one or more deuterium atoms;

$R^8$ is hydrogen, deuterium, $C_1$-$C_6$ alkyl, or benzyl, wherein said alkyl and benzyl each may optionally comprise one or more deuterium atoms;

$R^9$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{10}$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{11}$ is hydrogen, deuterium, $C_1$-$C_6$ alkyl, cycloalkyl, aryl, heteroaryl, or heterocyclyl, wherein said alkyl, cycloalkyl, aryl, heteroaryl, and heterocyclyl each may optionally comprise one or more deuterium atoms;

$R^{12}$ is $C_1$-$C_6$ alkyl, $C_3$-$C_6$ cycloalkyl, aryl, heteroaryl, or $NR^cR^d$, wherein said alkyl, cycloalkyl, aryl, and heteroaryl each may optionally comprise one or more deuterium atoms;

$R^{13}$ is $C_3$-$C_6$ cycloalkyl optionally substituted by one or more substituents independently selected from halogen, $C_1$-$C_6$ alkyl, $C_1$-$C_6$ alkoxy, oxo, or —$C(O)NR^cR^d$ and optionally comprising one or more deuterium atoms;

$R^{20}$ is aryl or heteroaryl, each optionally comprising one or more deuterium atoms;

$R_{aa}$, $R_{ab}$, $R_{ba}$, $R_{bb}$, $R_{ca}$, $R_{cb}$, $R_{da}$, and $R_{db}$ are each independently hydrogen or deuterium;

$R_{ea}$, $R_{eb}$, $R_{ec}$, $R_{fa}$, $R_{fb}$, and $R_{fc}$ are each independently selected from hydrogen, deuterium, $C_1$-$C_4$ alkyl, and —$OR^{22}$; and $R^{22}$ is selected from $C_1$-$C_6$ alkyl, $C_3$-$C_6$ cycloalkyl, heterocyclyl, aryl, and heteroaryl, each optionally comprising one or more deuterium atoms;

L is $C_1$-$C_4$ alkylene optionally comprising one or more deuterium atoms;

$L^5$ is methylene or ethylene, each optionally comprising one or more deuterium atoms;

$R^a$ and $R^b$ are independently selected from hydrogen, deuterium, alkyl, alkenyl, alkynyl, aryl, heteroaryl, and benzyl, wherein said alkyl, alkenyl, alkynyl, aryl, heteroaryl, and benzyl each may optionally comprise one or more deuterium atoms; and $R^c$ and $R^d$ are each independently hydrogen, deuterium, $C_1$-$C_6$ alkyl, benzyl, or aryl wherein said alkyl, aryl, and benzyl each may optionally comprise one or more deuterium atoms;

wherein any said aryl, heteroaryl, and benzyl each may optionally be substituted with one to five substituents independently selected from $C_1$-$C_6$ alkyl, $C_1$-$C_4$ haloalkyl, $C_1$-$C_6$ alkoxy, $C_1$-$C_4$ haloalkoxy, halogen, hydroxyl, cyano, and nitro;

wherein any said carbocyclyl, cycloalkyl, or heterocyclyl may optionally be substituted with one or more substituents independently selected from $C_1$-$C_6$ alkyl, $C_1$-$C_4$ haloalkyl, $C_1$-$C_6$ alkoxy, halogen, hydroxyl, and oxo;

wherein each said alkyl, haloalkyl, alkoxy, haloalkoxy, and hydroxyl each may optionally comprise one or more deuterium atoms; and wherein at least one of $R^1$ to $R^5$, $R^x$, $R_{aa}$, $R_{ab}$, $R_{ba}$, $R_{bb}$, $R_{ca}$, $R_{cb}$, $R_{da}$, $R_{db}$, $R_{ea}$, $R_{eb}$, $R_{ec}$, $R_{fa}$, $R_{fb}$, or $R_{fc}$ comprises one or more deuterium atoms, provided that when $R^1$ is selected from hydrogen, deuterium, halogen, —OH, —$OCD_3$, and —$OCH_3$, then $R^2$ is not hydrogen, deuterium, halogen, $CF_3$, —C≡CH or —C≡CD.

In another embodiment of the first aspect, the present disclosure provides a compound of Formula (Ia), or a stereoisomer, a prodrug, or a pharmaceutically acceptable salt or solvate thereof, wherein $R_{aa}$, $R_{ab}$, $R_{ba}$, $R_{bb}$, $R_{ca}$, $R_{cb}$, $R_{da}$, $R_{db}$, $R_{ea}$, $R_{eb}$, $R_{ec}$, $R_{fa}$, $L_{fb}$, and $R_{fc}$ are each independently hydrogen or deuterium.

In another embodiment of the first aspect, the present disclosure provides a compound of Formula (Ia), or a stereoisomer, a prodrug, or a pharmaceutically acceptable salt or solvate thereof, wherein:

$R_{aa}$ and $R_{ab}$ are the same and are hydrogen or deuterium;
$R_{ba}$ and $R_{bb}$ are the same and are hydrogen or deuterium;
$R_{ca}$ and $R_{cb}$ are the same and are hydrogen or deuterium;
$R_{da}$ and $R_{db}$ are the same and are hydrogen or deuterium;
$R_{ea}$, $R_{eb}$, and $R_{ec}$ are the same and are hydrogen or deuterium; and
$R_{fa}$, $R_{fb}$, and $R_{fc}$ are the same and are hydrogen or deuterium.

In another embodiment of the first aspect, the present disclosure provides a compound of Formula (Ia), or a stereoisomer, a prodrug, or a pharmaceutically acceptable salt or solvate thereof, wherein:

$R^1$ is selected from hydrogen, deuterium, halogen, —$OR^7$, and —$NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^7$ is hydrogen, deuterium, $C_1$-$C_4$ alkyl optionally comprising one or more deuterium atoms, or -$L^5$-$R^{20}$;

$R^{13}$ is $C_3$-$C_6$ cycloalkyl optionally substituted by —C(O)NR$^c$R$^d$;

$L^5$ is methylene or ethylene, each optionally comprising one or more deuterium atoms;

$R^{20}$ is aryl or heteroaryl, each optionally substituted with one or more substituents independently selected from halogen, $C_1$-$C_4$ alkyl, and $C_1$-$C_4$ alkoxy;

$R^c$ and $R^d$ are each independently hydrogen, deuterium, $C_1$-$C_6$ alkyl, benzyl, or aryl optionally substituted by one or more substituents independently selected from deuterium, halogen, $C_1$-$C_4$ alkyl, and $C_1$-$C_4$ alkoxy;

$R_{aa}$, $R_{ab}$, $R_{ba}$, $R_{bb}$, $R_{ca}$, $R_{cb}$, $R_{da}$, and $R_{db}$ are each hydrogen; and $R_{ea}$, $R_{eb}$, $R_{ec}$, $R_{fa}$, $R_{fb}$, and $R_{fc}$ are each independently hydrogen or deuterium.

In another embodiment of the first aspect, the present disclosure provides a compound of Formula (Ia), or a stereoisomer, a prodrug, or a pharmaceutically acceptable salt or solvate thereof, wherein:

$R^1$ is selected from hydrogen, deuterium, F, Cl,

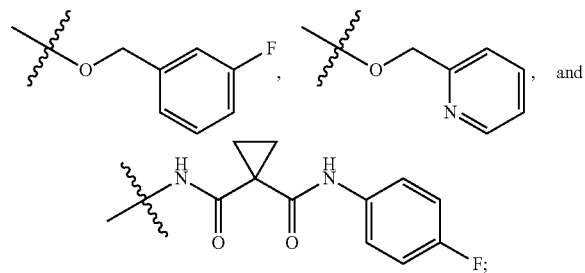

$R^2$ and $R^4$ are each independently selected from hydrogen, deuterium, F, Cl, —C≡CH, —C≡CD, and —CN;

$R^3$ and $R^5$ are each independently selected from hydrogen, deuterium, and F;

X is selected from —OCH$_2$CH$_2$OCH$_3$, —OCH$_2$CD$_2$OCH$_3$, —OCH$_2$CH$_2$OCD$_3$, and —OCH$_2$CH$_2$OCD$_2$CH$_3$; and Y is selected from hydrogen, deuterium, —OCH$_3$, —OCD$_3$, —OCH$_2$CH$_3$, —OCD$_2$CH$_3$, —OCD$_2$CD$_3$, —OCH$_2$CH$_2$OCH$_3$, —OCH$_2$CD$_2$OCH$_3$, —OCH$_2$CH$_2$OCD$_3$, and —OCH$_2$CH$_2$OCD$_2$CH$_3$.

In another embodiment of the first aspect, the present disclosure provides a compound of Formula (I), or a stereoisomer, a prodrug, or a pharmaceutically acceptable salt or solvate thereof, wherein X and Y are each independently —OR$^{14}$ or —O-L$^1$-R$^{15}$, wherein:

$R^{14}$ is selected from H, deuterium, $C_1$-$C_6$ alkyl, carbocyclyl, heterocyclyl, and -L$^2$-O—R$^{18}$, wherein said carbocyclyl and heterocyclyl each may optionally be substituted by one or more substituents independently selected from halogen, $C_1$-$C_4$ alkyl, $C_1$-$C_4$ alkoxy, and oxo, wherein each said alkyl, alkoxy, carbocyclyl, and heterocyclyl may optionally comprise one or more deuterium atoms;

$R^{15}$ is selected from hydrogen, deuterium, $C_1$-$C_4$ alkyl, carbocyclyl, heterocyclyl, and —OR$^{21}$, wherein said alkyl, carbocyclyl, and heterocyclyl may optionally be substituted by one or more substituents independently selected from halogen, $C_1$-$C_4$ alkyl, $C_1$-$C_4$ alkoxy, and oxo, wherein said alkyl, alkoxy, carbocyclyl, and heterocyclyl each may optionally comprise one or more deuterium atoms;

$R^{18}$ and $R^{21}$ are each independently $C_1$-$C_6$ alkyl optionally comprising one or more deuterium atoms; and $L^2$ is ethylene optionally comprising one or two deuterium atoms.

In another embodiment of the first aspect, the present disclosure provides a compound of Formula (I), or a stereoisomer, a prodrug, or a pharmaceutically acceptable salt or solvate thereof, wherein X and Y are each independently —OR$^{14}$ or —O-L$^1$-R$^{15}$, wherein:

$R^{14}$ is selected from H, deuterium, $C_1$-$C_6$ alkyl, carbocyclyl, heterocyclyl, and -L$^2$-O—R$^{18}$, wherein said carbocyclyl and heterocyclyl each may optionally be substituted by one or more substituents independently selected from halogen, $C_1$-$C_4$ alkyl, $C_1$-$C_4$ alkoxy, and oxo, wherein each said alkyl, alkoxy, carbocyclyl, and heterocyclyl may optionally comprise one or more deuterium atoms;

$R^{15}$ is —OR$^{21}$ or heterocycyl optionally comprising one or more deuterium atoms;

$R^{18}$ is $C_1$-$C_6$ alkyl optionally comprising one or more deuterium atoms;

$R^{21}$ is $C_1$-$C_4$ alkyl optionally comprising one or more deuterium atoms;

$L^1$ is $C_1$-$C_4$ alkylene optionally comprising one or more deuterium atoms; and $L^2$ is ethylene optionally comprising one or two deuterium atoms.

In another embodiment of the first aspect, the present disclosure provides a compound of Formula (I), or a stereoisomer, a prodrug, or a pharmaceutically acceptable salt or solvate thereof, wherein X and Y are each independently —OR$^{14}$ or —O-L$^1$-R$^{15}$, wherein:

$R^1$ is selected from hydrogen, deuterium, halogen, —OR$^7$, and —NHC(O)R$^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^x$ is hydrogen or deuterium;

$R^7$ is hydrogen, deuterium, $C_1$-$C_4$ alkyl, aryl, heteroaryl, or -$L^5$-$R^{20}$, wherein said alkyl, aryl, or heteroaryl may optionally comprise one or more deuterium atoms;

$R^{13}$ is $C_3$-$C_6$ cycloalkyl optionally substituted by —C(O)NR$^c$R$^d$ and optionally comprising one or more deuterium atoms;

$R^{14}$ is selected from H, deuterium, $C_1$-$C_6$ alkyl, carbocyclyl, heterocyclyl, and -L$^2$-O—R$^{18}$, wherein said carbocyclyl and heterocyclyl each may optionally be substituted by one or more substituents independently selected from halogen, $C_1$-$C_4$ alkyl, $C_1$-$C_4$ alkoxy, and oxo, wherein each said alkyl, alkoxy, carbocyclyl, and heterocyclyl may optionally comprise one or more deuterium atoms;

$R^{15}$ is —OR$^{21}$ or heterocycyl optionally comprising one or more deuterium atoms;

$R^{18}$ is $C_1$-$C_6$ alkyl optionally comprising one or more deuterium atoms;

$R^{20}$ is aryl or heteroaryl, each optionally substituted with one or more substituents independently selected from halogen, $C_1$-$C_4$ alkyl, $C_1$-$C_4$ haloalkyl, $C_1$-$C_4$ alkoxy, cyano, and nitro and each optionally comprising one or more deuterium atoms;

$R^{21}$ is $C_1$-$C_4$ alkyl optionally comprising one or more deuterium atoms.

$L^1$ is $C_1$-$C_4$ alkylene optionally comprising one or more deuterium atoms;

$L^2$ is ethylene optionally comprising one or two deuterium atoms;

$L^5$ is methylene or ethylene, each optionally comprising one or more deuterium atoms; and $R^c$ and $R^d$ are each independently hydrogen, deuterium, $C_1$-$C_6$ alkyl, benzyl, or aryl wherein said alkyl, aryl, and benzyl each may optionally comprise one or more deuterium atoms.

In another embodiment of the first aspect, the present disclosure provides a compound of Formula (Ib) or (Ic):

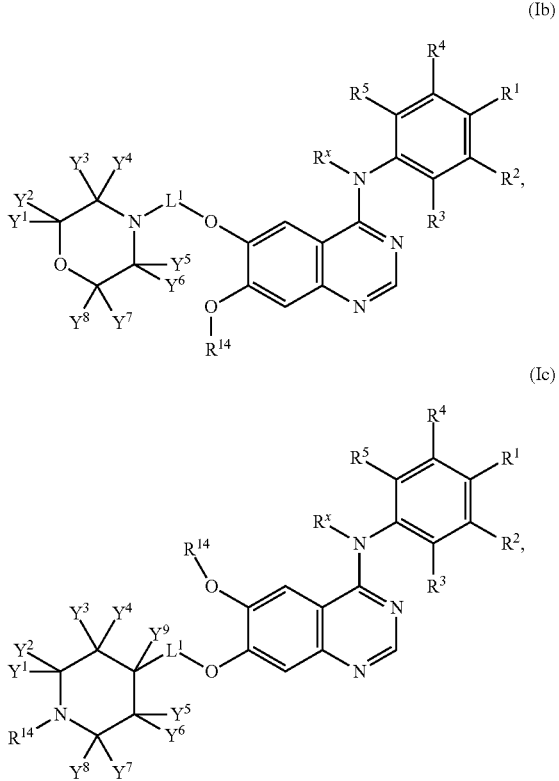

or a stereoisomer, a prodrug, or a pharmaceutically acceptable salt or solvate thereof, wherein:

$R^1$ is selected from hydrogen, deuterium, halogen, —$OR^7$, and —$NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^x$ is hydrogen or deuterium;

$R^7$ is hydrogen, deuterium, $C_1$-$C_4$ alkyl, aryl, heteroaryl, or -$L^5$-$R^{20}$, wherein said alkyl, aryl, or heteroaryl may optionally comprise one or more deuterium atoms;

$R^{13}$ is $C_3$-$C_6$ cycloalkyl optionally substituted by —$C(O)NR^cR^d$ and optionally comprising one or more deuterium atoms;

$R^{14}$ is selected from H, deuterium, $C_1$-$C_6$ alkyl, carbocyclyl, heterocyclyl, and -$L^2$-O—$R^{18}$, wherein said carbocyclyl and heterocyclyl each may optionally be substituted by one or more substituents independently selected from halogen, $C_1$-$C_4$ alkyl, $C_1$-$C_4$ alkoxy, and oxo, wherein each said alkyl, alkoxy, carbocyclyl, and heterocyclyl may optionally comprise one or more deuterium atoms;

$R^{18}$ is $C_1$-$C_6$ alkyl optionally comprising one or more deuterium atoms;

$R^{20}$ is aryl or heteroaryl, each optionally substituted with one or more substituents independently selected from halogen, $C_1$-$C_4$ alkyl, $C_1$-$C_4$ haloalkyl, $C_1$-$C_4$ alkoxy, cyano, and nitro and each optionally comprising one or more deuterium atoms;

$L^1$ is $C_2$-$C_4$ alkylene optionally comprising one or more deuterium atoms;

$L^2$ is ethylene optionally comprising one or two deuterium atoms;

$L^5$ is methylene or ethylene, each optionally comprising one or more deuterium atoms;

$R^c$ and $R^d$ are each independently hydrogen, deuterium, $C_1$-$C_6$ alkyl, benzyl, or aryl wherein said alkyl, aryl, and benzyl each may optionally comprise one or more deuterium atoms; and $Y^1$, $Y^2$, $Y^3$, $Y^4$, $Y^5$, $Y^6$, $Y^7$, $Y^8$, and $Y^9$ are each independently hydrogen or deuterium; wherein at least one of $R^1$, $R^2$, $R^3$, $R^4$, $R^5$, $R^x$, $R^{14}$, $Y^1$, $Y^2$, $Y^3$, $Y^4$, $Y^5$, $Y^6$, $Y^7$, $Y^8$, or $Y^9$ comprises one or more deuterium atoms, Provided (1) that for formula (Ib), when either one of $R^2$ or $R^4$ is chloro, then $R^{14}$ is not hydrogen, methyl, or deuterated methyl; and (2) that for formula (Ic), when $L^1$ is methylene or deuterated methylene, $R^1$ is bromo and either $R^3$ or $R^5$ is fluoro, then $R^{14}$ is not methyl or deuterated methyl.

In another embodiment of the first aspect, the present disclosure provides a compound of Formula (Ib) or (Ic), or a stereoisomer, a prodrug, or a pharmaceutically acceptable salt or solvate thereof, wherein:

$R^1$ is selected from hydrogen, deuterium, halogen, —$OR^7$, and —$NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^7$ is hydrogen, deuterium, $C_1$-$C_4$ alkyl optionally comprising one or more deuterium atoms, or -$L^5$-$R^{20}$;

$R^{13}$ is cyclopropyl optionally substituted by —$C(O)NR^cR^d$;

$R^{14}$ is selected from H, deuterium, $C_1$-$C_6$ alkyl, carbocyclyl, heterocyclyl, and -$L^2$-O—$R^{18}$, wherein said carbocyclyl and heterocyclyl each may optionally be substituted by one or more substituents independently selected from halogen, $C_1$-$C_4$ alkyl, $C_1$-$C_4$ alkoxy, and oxo, wherein each said alkyl, alkoxy, carbocyclyl, and heterocyclyl may optionally comprise one or more deuterium atoms;

$R^{18}$ is methyl or ethyl, each optionally comprising one or more deuterium atoms;

$R^{20}$ is aryl or heteroaryl, each optionally substituted with one or more substituents independently selected from halogen, $C_1$-$C_4$ alkyl, $C_1$-$C_4$ alkoxy, cyano, and nitro, and each optionally comprising one or more deuterium atoms;

$L^1$ is n-propylene optionally comprising one to six deuterium atoms;

$L^2$ is ethylene optionally comprising one or two deuterium atoms;

$L^5$ is methylene or ethylene, each optionally comprising one or more deuterium atoms; and $R^c$ and $R^d$ are each independently hydrogen, deuterium, $C_1$-$C_4$ alkyl, benzyl, or aryl optionally substituted by one or more substituents independently selected from halogen, $C_1$-$C_4$ alkyl, $C_1$-$C_4$ haloalkyl, $C_1$-$C_4$ alkoxy, cyano, and nitro, wherein each said alkyl, benzyl, aryl, haloaryl, and alkoxy may optionally comprise one or more deuterium atoms.

In another embodiment of the first aspect, the present disclosure provides a compound of Formula (Ib) or (Ic), or a stereoisomer, a prodrug, or a pharmaceutically acceptable salt or solvate thereof, wherein:

$R^1$ is selected from hydrogen, deuterium, F, Cl,

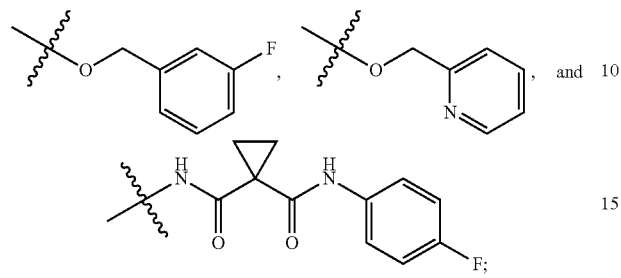

$R^2$ and $R^4$ are each independently hydrogen, deuterium, F, Cl, —C≡CH or —C≡CD;

$R^3$ and $R^5$ are each independently hydrogen, deuterium, or F;

$R^{14}$ is methyl optionally comprising one to three deuterium atoms, or -L$^2$-O—R$^{18}$;

$L^2$ is ethylene optionally comprising one to four deuterium atoms; and $R^{18}$ is methyl optionally comprising one to three deuterium atoms.

In another embodiment of the first aspect, the present disclosure provides a compound of Formula (Id):

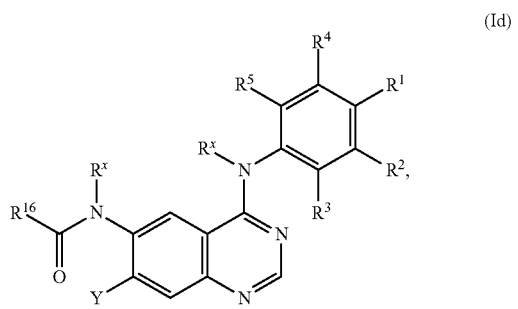

(Id)

or a stereoisomer, a prodrug, or a pharmaceutically acceptable salt or solvate thereof, wherein:

$R^x$, at each occurrence, is independently hydrogen or deuterium;

Y is selected from —OR$^{14}$ and —O-L$^1$-R$^{15}$;

$R^{14}$ is selected from H, deuterium, $C_1$-$C_6$ alkyl, carbocyclyl, heterocyclyl, and -L$^2$-O—R$^{18}$, wherein said carbocyclyl and heterocyclyl each may optionally be substituted by one or more substituents independently selected from halogen, $C_1$-$C_4$ alkyl, $C_1$-$C_4$ alkoxy, and oxo, and wherein each said alkyl, alkoxy, carbocyclyl, and heterocyclyl may optionally comprise one or more deuterium atoms;

$L^1$ is $C_1$-$C_3$ alkylene optionally comprising one or more deuterium atoms;

$L^2$ is ethylene optionally comprising one or more deuterium atoms;

$R^{15}$ is selected from hydrogen, deuterium, $C_1$-$C_4$ alkyl, carbocyclyl, heterocyclyl, or —OR$^{21}$, wherein said alkyl, carbocyclyl or heterocyclyl each may optionally be substituted by one or more substituents independently selected from halogen, $C_1$-$C_4$ alkyl, $C_1$-$C_4$ alkoxy, and oxo, and wherein each said alkyl, alkoxy, carbocyclyl, and heterocyclyl may optionally comprise one or more deuterium atoms;

$R^{16}$ is selected from

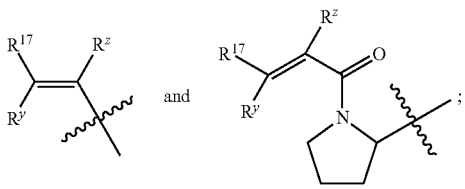

$R^y$ and $R^z$ are each independently hydrogen or detuerium;

$R^{17}$ is selected from hydrogen, deuterium, and -L-NR$^e$R$^f$;

$R^{18}$ is -L$^5$-O—R$^{22}$ or $C_1$-$C_6$ alkyl optionally comprising one or more deuterium atoms;

L is methylene or ethylene, each optionally comprising one or more deuterium atoms;

$L^5$ is methylene or ethylene, each optionally comprising one or more deuterium atoms;

$R^{19}$ is $C_1$-$C_6$ alkyl optionally comprising one or more deuterium atoms;

$R^{20}$ is aryl or heteroaryl, each optionally substituted with one or more substituents independently selected from halogen, $C_1$-$C_4$ alkyl, $C_1$-$C_4$ haloalkyl, $C_1$-$C_4$ alkoxy, cyano, and nitro, and each optionally comprising one or more deuterium atoms;

$R^{21}$ is $C_1$-$C_6$ alkyl optionally comprising one or more deuterium atoms;

$R^{22}$ is selected from $C_1$-$C_6$ alkyl, $C_3$-$C_6$ cycloalkyl, heterocyclyl, aryl, and heteroaryl, each optionally substituted by $C_1$-$C_6$ alkyl, wherein each said $C_1$-$C_6$ alkyl may optionally comprise one or more deuterium atoms;

$R^c$ and $R^d$ are each independently hydrogen, deuterium, $C_1$-$C_6$ alkyl, benzyl, or aryl optionally substituted by one or more substituents independently selected from deuterium, halogen, $C_1$-$C_4$ alkyl, or $C_1$-$C_4$ alkoxy; and $R^e$ and $R^f$ are each independently hydrogen, deuterium, or $C_1$-$C_4$ alkyl optionally comprising one or more deuterium atoms;

wherein each said aryl, heteroaryl, and phenyl group of benzyl may optionally be substituted with one to five substituents independently selected from $C_1$-$C_6$ alkyl, $C_1$-$C_4$ haloalkyl, $C_1$-$C_6$ alkoxy, $C_1$-$C_4$ haloalkoxy, halogen, hydroxyl, cyano, and nitro;

wherein each said carbocyclyl, cycloalkyl, or heterocyclyl may optionally be substituted with one or more substituents independently selected from $C_1$-$C_6$ alkyl, $C_1$-$C_4$ haloalkyl, $C_1$-$C_6$ alkoxy, halogen, hydroxyl, and oxo; and wherein at least one of $R^1$, $R^2$, $R^3$, $R^4$, $R^5$, $R^x$, $R^{16}$, or Y comprises one or more deuterium atoms.

In another embodiment of the first aspect, the present disclosure provides a compound of Formula (Id), wherein $R^{16}$ is

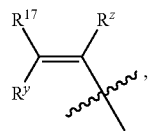

further characterized by formula (Ie):

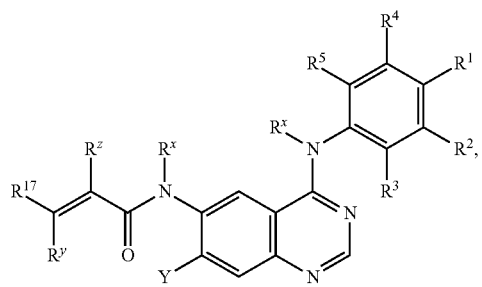

or a stereoisomer, a prodrug, or a pharmaceutically acceptable salt or solvate thereof, wherein:

$R^1$ is selected from hydrogen, deuterium, halogen, $-OR^7$, and $-NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^y$ and $R^z$ are each independently hydrogen or deuterium;

$R^7$ is hydrogen, deuterium, or $C_1$-$C_4$ alkyl optionally comprising one or more deuterium atoms, or -$L^5$-$R^{20}$;

$R^{13}$ is $C_3$-$C_6$ cycloalkyl optionally substituted by $-C(O)NR^cR^d$;

$L^5$ is methylene or ethylene, each optionally comprising one or more deuterium atoms;

$R^{17}$ is selected from hydrogen, deuterium, and -L-$NR^eR^f$;

L is methylene optionally comprising one or two deuterium atoms;

$R^{20}$ is aryl or heteroaryl, each optionally substituted with one or more substituents independently selected from halogen, $C_1$-$C_4$ alkyl, and $C_1$-$C_4$ alkoxy;

$R^c$ and $R^d$ are each independently hydrogen, deuterium, $C_1$-$C_6$ alkyl, benzyl, or aryl optionally substituted by one or more substituents independently selected from deuterium, halogen, $C_1$-$C_4$ alkyl, or $C_1$-$C_4$ alkoxy; and $R^e$ and $R^f$ are each independently hydrogen, deuterium, or $C_1$-$C_4$ alkyl optionally comprising one or more deuterium atoms;

wherein each said aryl, heteroaryl, and phenyl group of benzyl may optionally be substituted with one to five substituents independently selected from $C_1$-$C_6$ alkyl, $C_1$-$C_4$ haloalkyl, $C_1$-$C_6$ alkoxy, $C_1$-$C_4$ haloalkoxy, halogen, hydroxyl, cyano, and nitro;

wherein each said carbocyclyl, cycloalkyl, or heterocyclyl may optionally be substituted with one or more substituents independently selected from $C_1$-$C_6$ alkyl, $C_1$-$C_4$ haloalkyl, $C_1$-$C_6$ alkoxy, halogen, hydroxyl, and oxo; and wherein at least one of $R^1$, $R^2$, $R^3$, $R^4$, $R^5$, $R^z$, $R^y$, $R^{17}$, or Y comprises one or more deuterium atoms.

In another embodiment of the first aspect, the present disclosure provides a compound of Formula (Ie), wherein:

$R^1$ is selected from hydrogen, deuterium, F, Cl,

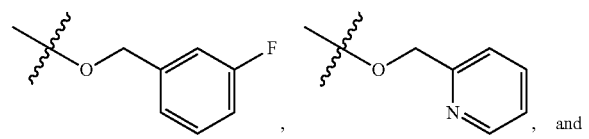, and

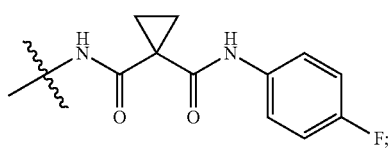

$R^2$ and $R^4$ are each independently selected from hydrogen, deuterium, F, Cl, $-C\equiv CH$, and $-C\equiv CD$;

$R^3$ and $R^5$ are each independently selected from hydrogen, deuterium, and F;

$R^{17}$, $R^y$, and $R^z$ are each independently hydrogen or deuterium; and

Y is selected from hydrogen, deuterium, $-OCH_3$, $-OCD_3$, $-OCH_2CH_3$, $-OCD_2CH_3$, $-OCD_2CD_3$, $-OCH_2CH_2OCH_3$, $-OCH_2CD_2OCH_3$, $-OCH_2CH_2OCD_3$,

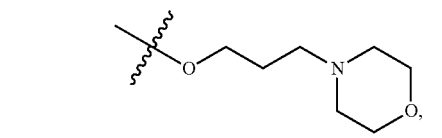

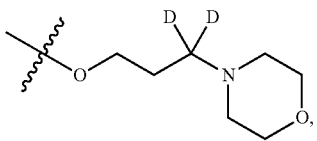

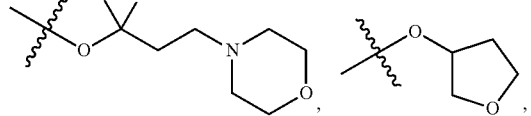

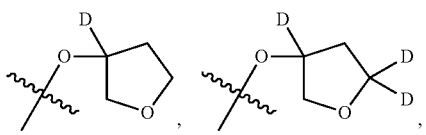

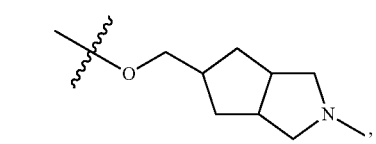

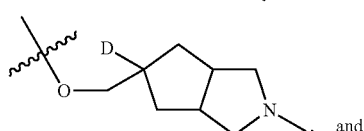, and

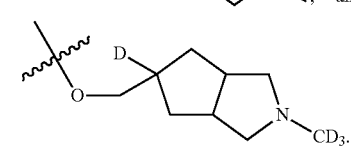

In another embodiment of the first aspect, the present disclosure provides a compound of Formula (Ie), wherein $R^{17}$, $R^y$, and $R^z$ are each hydrogen.

In another embodiment of the first aspect, the present disclosure provides a compound of Formula (Id), wherein $R^{17}$ is $-C(R^pR^q)-NR^eR^f$, further characterized by formula (If):

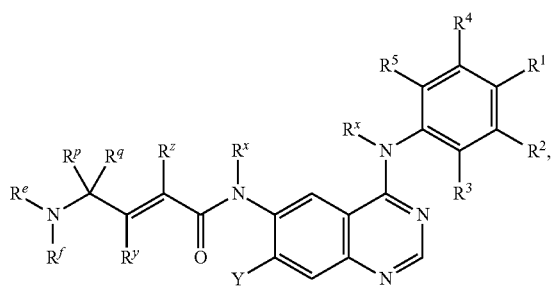

(If)

or a stereoisomer, a prodrug, or a pharmaceutically acceptable salt or solvate thereof, wherein:

$R^x$, at each occurrence, is independently hydrogen or deuterium;

$R^y$ and $R^z$ are each independently hydrogen or deuterium;

$R^p$ and $R^q$ are each independently hydrogen or deuterium;

$R^1$ is selected from hydrogen, deuterium, halogen, —$OR^7$, and —$NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^7$ is hydrogen, deuterium, or $C_1$-$C_4$ alkyl optionally comprising one or more deuterium atoms, or -$L^5$-$R^{20}$;

$R^{13}$ is cyclopropyl optionally substituted by —C(O)$NR^cR^d$;

$L^5$ is methylene or ethylene, each optionally comprising one or more deuterium atoms;

$R^{20}$ is aryl or heteroaryl, each optionally substituted with one or more substituents independently selected from halogen, $C_1$-$C_4$ alkyl, and $C_1$-$C_4$ alkoxy;

$R^c$ and $R^d$ are each independently hydrogen, deuterium, $C_1$-$C_6$ alkyl, benzyl, or aryl optionally substituted by one or more substituents independently selected from deuterium, halogen, $C_1$-$C_4$ alkyl, or $C_1$-$C_4$ alkoxy; and $R^e$ and $R^f$ are each independently hydrogen, deuterium, or $C_1$-$C_4$ alkyl optionally comprising one or more deuterium atoms;

wherein at least one of $R^1$, $R^2$, $R^3$, $R^4$, $R^5$, $R^e$, $R^f$, $R^x$, $R^y$, $R^z$, $R^p$, $R^q$, or Y comprises one or more deuterium atoms.

In another embodiment of the first aspect, the present disclosure provides a compound of Formula (If), or a stereoisomer, a prodrug, or a pharmaceutically acceptable salt or solvate thereof, wherein:

$R^1$ is selected from hydrogen, deuterium, F, Cl,

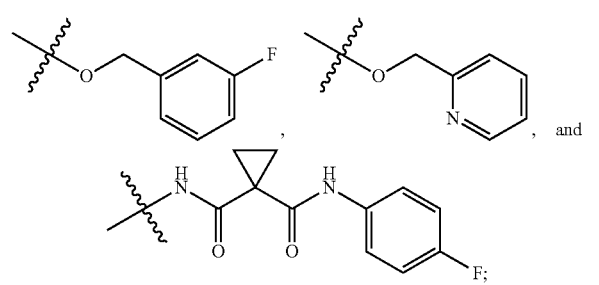

$R^2$ and $R^4$ are each independently selected from hydrogen, deuterium, F, Cl, —C≡CH, and —C≡CD;

$R^3$ and $R^5$ are each independently selected from hydrogen, deuterium, and F;

Y is selected from hydrogen, deuterium, —$OCH_3$, —$OCD_3$, —$OCH_2CH_3$, —$OCD_2CH_3$, —$OCD_2CD_3$, —$OCH_2CH_2OCH_3$, —$OCH_2CD_2OCH_3$, —$OCH_2CH_2OCD_3$,

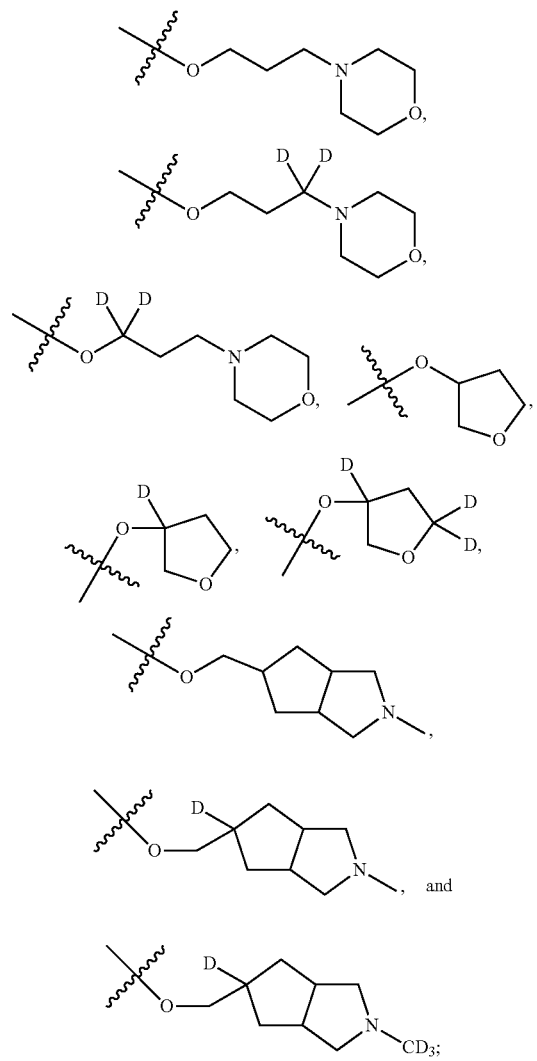

$R^x$, at each occurrence, is independently hydrogen or deuterium;

$R^y$ and $R^z$ are each independently hydrogen or deuterium;

$R^e$ and $R^f$ are each independently $CH_3$ or $CD_3$; and $R^p$ and $R^q$ are each independently hydrogen or deuterium;

wherein at least one of $R^1$, $R^2$, $R^3$, $R^4$, $R^5$, $R^e$, $R^f$, $R^x$, $R^y$, $R^z$, $R^p$, $R^q$, or Y comprises one or more deuterium atoms.

In another embodiment of the first aspect, the present disclosure provides a compound of Formula (If), or a stereoisomer, a prodrug, or a pharmaceutically acceptable salt or solvate thereof, wherein:

$R^p$, $R^q$, $R^y$, and $R^z$ are each hydrogen.

In another embodiment of the first aspect, the present disclosure provides a compound of Formula (Id), wherein $R^{16}$ is

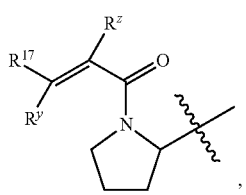

further characterized by Formula (Ig):

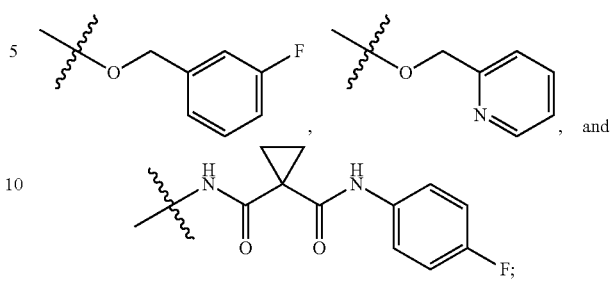

(Ig)

or a stereoisomer, a prodrug, or a pharmaceutically acceptable salt or solvate thereof, wherein:

$R^y$ and $R^z$ are each independently hydrogen or deuterium;

$R^1$ is selected from hydrogen, deuterium, halogen, —$OR^7$, and —$NHC(O)R^{13}$;

$R^2$ and $R^4$ are each independently hydrogen, deuterium, halogen, or $C_2$-$C_4$ alkynyl optionally comprising one or more deuterium atoms;

$R^3$ and $R^5$ are each independently hydrogen, deuterium, or halogen;

$R^{17}$ is hydrogen, deuterium, or -L-$NR^eR^f$;

$R^7$ is hydrogen, deuterium, $C_1$-$C_4$ alkyl optionally comprising one or more deuterium atoms, or -$L^5$-$R^{20}$;

$R^{13}$ is cyclopropyl optionally substituted by —C(O)$NR^cR^d$;

$R^{20}$ is aryl or heteroaryl, each optionally substituted with one or more substituents independently selected from halogen, $C_1$-$C_4$ alkyl, and $C_1$-$C_4$ alkoxy;

L is methylene optionally comprising one or more deuterium atoms;

$L^5$ is methylene or ethylene, each optionally comprising one or more deuterium atoms;

$R^c$ and $R^d$ are each independently hydrogen, deuterium, $C_1$-$C_6$ alkyl, benzyl, or aryl optionally substituted by one or more substituents independently selected from deuterium, halogen, $C_1$-$C_4$ alkyl, or $C_1$-$C_4$ alkoxy, and wherein each said alkyl, benzyl, aryl, and alkoxy each may optionally comprise one or more deuterium atoms; and $R^e$ and $R^f$ are each independently hydrogen, deuterium, or $C_1$-$C_4$ alkyl optionally comprising one or more deuterium atoms;

wherein at least one of $R^1$, $R^2$, $R^3$, $R^4$, $R^5$, $R^x$, $R^y$, $R^z$, $R^{17}$, or Y comprises one or more deuterium atoms.

In another embodiment of the first aspect, the present disclosure provides a compound of Formula (Ig), or a stereoisomer, a prodrug, or a pharmaceutically acceptable salt or solvate thereof, wherein:

$R^1$ is selected from hydrogen, deuterium, F, Cl,

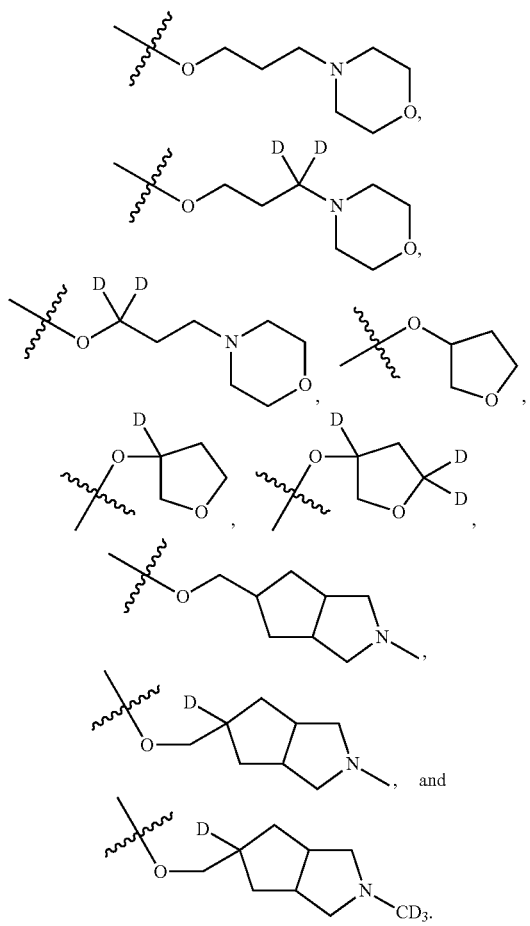

$R^2$ and $R^4$ are each independently selected from hydrogen, deuterium, F, Cl, —C≡CH, and —C≡CD;

$R^3$ and $R^5$ are each independently selected from hydrogen, deuterium, and F;

$R^{17}$ is hydrogen, deuterium, or -L-$NR^eR^f$;

L is methylene optionally comprising one or more deuterium atoms;

$R^e$ and $R^f$ are each independently hydrogen, deuterium, or $C_1$-$C_4$ alkyl optionally comprising one or more deuterium atoms; and Y is selected from hydrogen, deuterium, —$OCH_3$, —$OCD_3$, —$OCH_2CH_3$, —$OCD_2CH_3$, —$OCD_2CD_3$, —$OCH_2CH_2OCH_3$, —$OCH_2CD_2OCH_3$, —$OCH_2CH_2OCD_3$, In another embodiment of the first aspect, the present disclosure provides a compound of Formula (Ig), or a stereoisomer, a prodrug, or a pharmaceutically acceptable salt or solvate thereof, wherein $R^{17}$ is hydrogen or deuterium.

In another embodiment of the first aspect, the present disclosure provides a compound of Formula (Ig), or a stereoisomer, a prodrug, or a pharmaceutically acceptable salt or solvate thereof, wherein $R^{17}$, $R^y$ and $R^z$ are each hydrogen.

In another embodiment of the first aspect, the present disclosure provides a compound of Formula (I), wherein X is a group of Formula (A), further characterized by Formula (Ih):

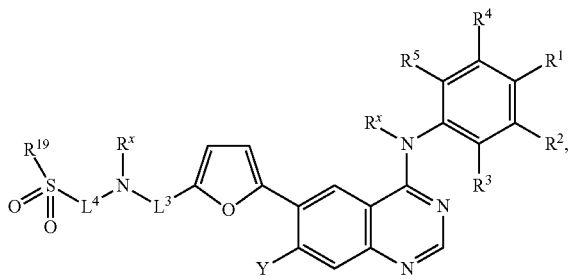

(Ih)

or a stereoisomer, a prodrug, or a pharmaceutically acceptable salt or solvate thereof, wherein:

Y is hydrogen, deuterium, —$OR^{14}$, or —O-$L^1$-$R^{15}$;

$R^{14}$ is selected from H, deuterium, $C_1$-$C_6$ alkyl, carbocyclyl, and heterocyclyl, wherein said carbocyclyl and heterocyclyl each may optionally be substituted by one or more substituents independently selected from halogen, $C_1$-$C_4$ alkyl, $C_1$-$C_4$ alkoxy, and oxo, and wherein each said alkyl, alkoxy, carbocyclyl, and heterocyclyl may optionally comprise one or more deuterium atoms; and $R^{15}$ is selected from hydrogen, deuterium, $C_1$-$C_4$ alkyl, carbocyclyl, heterocyclyl, and —$OR^{21}$, wherein said alkyl, carbocyclyl (definition), or heterocyclyl (definition) may optionally be substituted by one or more substituents independently selected from halogen, $C_1$-$C_4$ alkyl, $C_1$-$C_4$ alkoxy, and oxo, and wherein each said alkyl, carbocyclyl, heterocyclyl, and alkoxy may optionally comprise one or more deuterium atoms;

$R^{19}$ is $C_1$-$C_6$ alkyl optionally comprising one or more deuterium atoms;

$L^1$ is $C_1$-$C_3$ alkylene optionally comprising one or more deuterium atoms;

$L^3$ is methylene optionally comprising one or two deuterium atoms; and $L^4$ is ethylene optionally comprising one to four deuterium atoms;

wherein at least one of $R^1$, $R^2$, $R^3$, $R^4$, $R^5$, $R^{19}$, $R^z$, $L^3$, $L^4$, or Y comprises one or more deuterium atoms, provided that when Y is hydrogen or deuterium, $R^1$ is —$OR^7$, and $R^{19}$ is methyl or deuterated methyl, then $R^7$ is not 3-fluorobenzyl or deuterated 3-fluorobenzyl.

In another embodiment of the first aspect, the present disclosure provides a compound of Formula (Ih), or a stereoisomer or a pharmaceutically acceptable salt or solvate thereof, wherein:

$R^1$ is selected from hydrogen, deuterium, F, Cl,

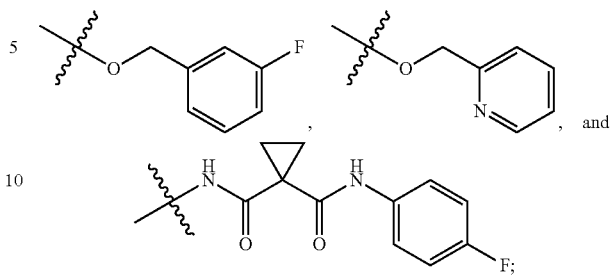

$R^2$ and $R^4$ are each independently selected from hydrogen, deuterium, F, Cl, —C≡CH, —C≡CD, and —CN;

$R^3$ and $R^5$ are each independently selected from hydrogen, deuterium, and F;

$R^{19}$ is methyl or ethyl, each optionally comprising one or more deuterium atoms; and Y is selected from hydrogen, deuterium, —$OCH_2CH_2OCH_3$, —$OCH_2CH_2OCD_3$, —$OCH_3$, —$OCD_3$, —$OCH_2CH_3$, and —$OCD_2CH_3$;

wherein at least one of $R^1$, $R^2$, $R^3$, $R^4$, $R^5$, $R^{19}$, $R^x$, $L^3$, $L^4$, or Y comprises one or more deuterium atoms.

In another embodiment of the first aspect, the present disclosure provides a compound of Formula (I), wherein X is a group of formula (B) and Y is —$OR^{14}$, further characterized by formula (II):

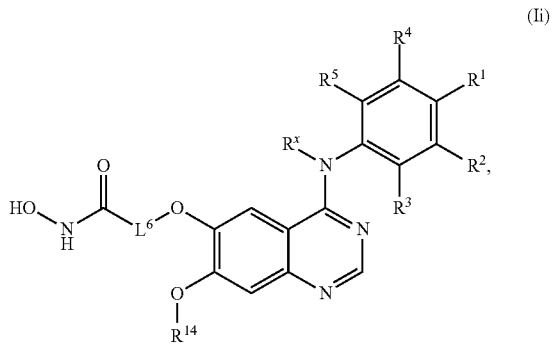

(Ii)

or a stereoisomer, a prodrug, or a pharmaceutically acceptable salt or solvate thereof, wherein $L^6$ is $C_1$-$C_{18}$ alkylene optionally comprising one or more deuterium atoms.

In a preferred embodiment of the first aspect, the present disclosure provides a compound of Formula (II), wherein:

$L^6$ is $C_1$-$C_{12}$ alkylene optionally comprising one or more deuterium atoms;

$R^2$ is —C≡CH or —C≡CD;

$R^{14}$ is hydrogen, deuterium, or $C_1$-$C_4$ alkyl optionally comprising one or more deuterium atoms; and $R^x$, $R^1$, $R^3$, $R^4$, and $R^5$ are each hydrogen or deuterium.

In another preferred embodiment of the first aspect, the present disclosure provides a compound of Formula (II), wherein $L^6$ is $C_2$-$C_8$ alkylene optionally comprising one or more deuterium atoms.

In another preferred embodiment of the first aspect, the present disclosure provides a compound, or a stereoisomer, a prodrug, or a pharmaceutically acceptable salt or solvate thereof, selected from the group consisting of:

(S,E)-N-(4-(3-chloro-4-fluorophenylamino)-7-(tetrahydrofuran-3-yloxy)quinazolin-6-yl)-4-($D_6$-dimethylamino)but-2-enamide;

(S,E)-4-($D_6$-dimethylamino)-N-(4-(3-ethynylphenylamino)-7-(tetrahydrofuran-3-yloxy)quinazolin-6-yl)but-2-enamide;

(E)- 4-(dimethylamino)-N-(4-(3-ethynylphenylamino)-7-((3-D)-tetrahydrofuran-3- yloxy)quinazolin-6-y1)but-2-enamide;

(E)-N-(4-(3-chloro-4-fluorophenylamino)-7- (3-D)-tetrahydrofuran-3-yloxy)quinazolin- 6-yl)-4-(dimethylamino)but-2-enamide;

7-(4-(3-ethynylphenylamino)-7-($D_3$-methoxy)quinazolin-6-yloxy)-N-hydroxyheptanamide;

N-(3-ethynylphenyl)-7-($D_3$-methoxy)-6-((2-methyl-octahydrocyclopenta[c]pyrrol-5-yl)methoxy)quinazolin-4-amine;

N-(3-ethynylphenyl)-7-(2-($D_3$-methoxy)ethoxy)-6-(tetrahydrofuran-3-yloxy)quinazolin-4-amine;

N-(3-ethynylphenyl)-7-($D_3$-methoxy)-6-(3-(morpholin-4-yl)propoxy)quinazolin-4-amine;

N-(4-chloro-3-fluorophenyl)-7-($D_3$-methoxy)-6-((2-methyl-octahydrocyclopenta[c]pyrrol-5-yl)methoxy)quinazolin-4-amine;

N-(3,4-dichloro-2-fluorophenyl)-7-($D_3$-methoxy)-6-(tetrahydrofuran-2-yloxy)quinazolin-4-amine;

N-(3-fluoro-4-(7-($D_3$-methoxy)-6-(3-(morpholin-4-yl)propoxy)quinazolin-4-ylamino)phenyl)-N-(4-fluorophenyl)cyclopropane-1,1-dicarboxamide;

N-(4-(6,7-bis(2-methoxyethoxy)quinazolin-4-(N-D)-ylamino)-3-fluorophenyl)-N-(4-fluorophenyl)cyclopropane-1,1-dicarboxamide;

N-(3,4-dichloro-2-fluorophenyl)-7-($D_3$-methoxy)-6-((2-methyl-octahydrocyclopenta[c]pyrrol-5-yl)methoxy)quinazolin-4-amine;

N-(3-chloro-4-(3-fluorobenzyloxy)phenyl)-7-($D_3$-methoxy)-6-(3-(morpholin-4-yl)propoxy)quinazolin-4-amine;

N-(3-chloro-4-(pyridin-2-ylmethoxy)phenyl)-6,7-bis(2-methoxyethoxy)quinazolin-4-(N-D)-amine;

N-(3-(2-D-ethynyl)phenyl)-6-(5-((2-(methylsulfonyl)ethylamino)methyl)furan-2-yl)quinazolin-4-amine;

N-(3-chloro-4-(pyridin-2-ylmethoxy)phenyl)-7-($D_3$-methoxy)-6-(5-((2-(methylsulfonyl)ethylamino)methyl)furan-2-yl)quinazolin-4-amine;

N-(3-ethynylphenyl)-7-methoxy-6-(5-((2-(methylsulfonyl)ethylamino)methyl)furan-2-yl)quinazolin-4-(N-D)-amine;

6-(5-((2-(ethylsulfonyl)ethylamino)methyl)furan-2-yl)-N-(3-(3-fluorobenzyloxy)phenyl)quinazolin-4-(N-D)-amine;

N-(3-chloro-4-fluorophenyl)-7-($D_3$-methoxy)-6-(5-((2-(methylsulfonyl)ethylamino)methyl)furan-2-yl)quinazolin-4-amine;

N-(3-chloro-4-(3-fluorobenzyloxy)phenyl)-7-($D_3$-methoxy)-6-(5-((2-(methylsulfonyl)ethylamino)methyl)furan-2-yl)quinazolin-4-amine;

(E)-N-(4-(3-chloro-4-fluorophenylamino)-7-($D_3$-methoxy)quinazolin-6-yl)-4-(dimethylamino)but-2-enamide;

(E)-4-(dimethylamino)-N-(4-(3-ethynylphenylamino)-7-($D_3$-methoxy)quinazolin-6-yl)but-2-enamide;

(E)-4-(dimethylamino)-N-(4-(3-ethynylphenylamino)-7-(1-D-tetrahydrofuran-3-yloxy)quinazolin-6-yl)but-2-enamide;

(E)-N-(4-(3-chloro-4-(3-fluorobenzyloxy)phenylamino)-7-($D_3$-methoxy)quinazolin-6-yl)-4-(dimethylamino)but-2-enamide;

(E)-N-(4-(3-chloro-2-fluoro-phenyl-(N-D)-amino)-7-methoxyquinazolin-6-yl)-4-(dimethylamino)but-2-enamide;

(E)-N-(4-(6-(4-(dimethylamino)but-2-enamido)-7-($D_3$-methoxy)quinazolin-4-ylamino)-3-fluorophenyl)-N-(4-fluorophenyl)cyclopropane-1,1-dicarboxamide;

(E)-N-(4-(3-chloro-4-(pyridin-2-ylmethoxy)phenyl-(N-D)-amino)-7-ethoxyquinazolin-6-yl)-4-(dimethylamino)but-2-enamide;

(E)-N-(4-(3-chloro-4-(3-fluorobenzyloxy)phenylamino)-7-(3,5,5-$D_3$-tetrahydrofuran-3-yloxy)quinazolin-6-yl)-4-(dimethylamino)but-2-enamide;

(E)-4-(dimethylamino)-N-(4-(3-(2-D-ethynyl)phenylamino)-7-(tetrahydrofuran-3-yloxy)quinazolin-6-yl)but-2-enamide;

(E)-N-(4-(3-chloro-4-fluorophenyl-(N-D)-amino)-7-((2-methyl-octahydrocyclopenta[c]pyrrol-5-yl)methoxy)quinazolin-6-yl)-4-(dimethylamino)but-2-enamide;

(E)-4-(dimethylamino)-N-(4-(3-(2-D-ethynyl)phenylamino)-7-((2-methyl-octahydrocyclopenta[c]pyrrol-5-yl)methoxy)quinazolin-6-yl)but-2-enamide;

(E)-N-(4-(3-chloro-4-(3-fluorobenzyloxy)phenyl-(N-D)-amino)-7-((2-methyl-octahydrocyclopenta[c]pyrrol-5-yl)methoxy)quinazolin-6-yl)-4-(dimethylamino)but-2-enamide;

N-(4-(3-chloro-4-fluorophenylamino)-7-($D_3$-methoxy)quinazolin-6-yl)acrylamide;

N-(4-(3-ethynylphenylamino)-7-($D_3$-methoxy)quinazolin-6-yl)acrylamide;

N-(4-(3-chloro-4-(pyridin-2-ylmethoxy)phenylamino)-7-($D_3$-methoxy)quinazolin-6-yl)acrylamide;

N-(4-(6-acrylamido-7-(1,1-$D_2$-3-(morpholin-4-yl)propoxy)quinazolin-4-ylamino)-3-fluorophenyl)-N-(4-fluorophenyl)cyclopropane-1,1-dicarboxamide;

N-(4-(3-chloro-4-fluorophenylamino)-7-(3-D-tetrahydrofuran-3-yloxy)quinazolin-6-yl)acrylamide;

N-(4-(3-chloro-4-(4-fluorobenzyloxy)phenylamino)-7-(3-D-tetrahydrofuran-3-yloxy)quinazolin-6-yl)acrylamide;

N-(4-(3-(2-D-ethynyl)phenylamino)-7-(tetrahydrofuran-3-yloxy)quinazolin-6-yl)acrylamide;

N-(4-(3-chloro-4-fluorophenyl-(N-D)-amino)-7-(2-methyl-octahydrocyclopenta[c]pyrrol-5-yloxy)quinazolin-6-yl)acrylamide;

N-(4-(3-(2-D-ethynyl)phenylamino)-7-((2-methyl-octahydrocyclopenta[c]pyrrol-5-yl)methoxy)quinazolin-6-yl)acrylamide;

1-acryloyl-N-(4-(3-chloro-4-fluorophenylamino)-7-($D_3$-methoxy)quinazolin-6-yl)pyrrolidine-2-carboxamide;

1-acryloyl-N-(4-(3-chloro-4-(3-fluorobenzyloxy)phenylamino)-7-(3-D-tetrahydrofuran-3-yloxy)quinazolin-6-yl)pyrrolidine-2-carboxamide;

N-(4-(6-(1-acryloylpyrrolidine-2-carboxamido)-7-($D_3$-methoxy)quinazolin-4-ylamino)-3-fluorophenyl)-N-(4-fluorophenyl)cyclopropane-1,1-dicarboxamide;

1-acryloyl-N-(4-(3-chloro-4-fluorophenylamino)-7-(1,1-$D_2$-3-(morpholin-4-yl)propoxy)quinazolin-6-yl)pyrrolidine-2-carboxamide;

1-acryloyl-N-(4-(3-(2-D-ethynyl)phenylamino)-7-(3-(morpholin-4-yl)propoxy)quinazolin-6-yl)pyrrolidine-2-carboxamide;

1-acryloyl-N-(4-(3-chloro-4-(pyridin-2-ylmethoxy)phenylamino)-7-(1,1-$D_2$-3-(morpholin-4-yl)propoxy)quinazolin-6-yl)pyrrolidine-2-carboxamide;

1-acryloyl-N-(4-(3-chloro-4-fluorophenyl-(N-D)-amino)-7-((2-methyl-octahydrocyclopenta[c]pyrrol-5-yl)methoxy)quinazolin-6-yl)pyrrolidine-2-carboxamide; and 1-acryloyl-N-(4-(3-ethynylphenyl-(N-D)-amino)-7-((2-methyl-octahydrocyclopenta[c]pyrrol-5-yl)methoxy)quinazolin-6-yl)pyrrolidine-2-carboxamide.

In a second aspect the present disclosure provides a composition comprising a compound of Formula (I), or a stereoisomer, a prodrug, or a pharmaceutically acceptable salt or solvate thereof, and a pharmaceutically acceptable carrier, wherein Formula (I) is defined according to any of the embodiments in the first aspect of the present invention as described above.

In one embodiment of the second aspect, the present disclosure provides a composition further comprising at least one additional compound having anti-hyperproliferative activity.

In another embodiment of the second aspect, the present disclosure provides a composition comprising a compound of Formula (I), or a stereoisomer, a prodrug, or a pharmaceutically acceptable salt or solvate thereof, and a pharmaceutically acceptable carrier, plus at least one additional compound having anti-hyperproliferative activity, wherein at least one of the additional compounds is effective to inhibit the activity of a receptor tyrosine kinase.

In another embodiment of the second aspect, the present disclosure provides a composition comprising a compound of Formula (I), or a stereoisomer, a prodrug, or a pharmaceutically acceptable salt or solvate thereof, and a pharmaceutically acceptable carrier, plus at least one additional compound having anti-hyperproliferative activity, wherein the at least one of the additional compounds is selected from inhibitors of epidermal growth factor receptor (EGFR) tyrosine kinase, HER1 tyrosine kinase, or HER2 tyrosine kinase.

In a third aspect the present disclosure provides a method of treating a hyperproliferative disease or disorder in a patient, comprising administering to the patient a therapeutically effective amount of a compound of Formula (I), or a stereoisomer, a prodrug, or a pharmaceutically acceptable salt or solvate thereof, wherein Formula (I) is defined according to any of the embodiments described above in the first aspect of the present disclosure.

In one embodiment of the third aspect, the method further comprises administering at least one additional compound having anti-hyperproliferative activity prior to, after, or simultaneously with the compound of Formula (I), or a pharmaceutically acceptable salt or solvate thereof.

In another embodiment of the third aspect, the present disclosure provides a method of treating a hyperproliferative disease or disorder in a patient, comprising administering to the patient a therapeutically effective amount of a compound of Formula (I), or a stereoisomer, a prodrug, or a pharmaceutically acceptable salt or solvate thereof, and at least one additional compound having anti-hyperproliferative activity prior to, after, or simultaneously with the compound of Formula (I), or a pharmaceutically acceptable salt or solvate thereof, wherein at least one of the additional compounds is effective to inhibit the activity of a tyrosine kinase.

In another embodiment of the third aspect, the present disclosure provides a method of treating a hyperproliferative disease or disorder in a patient, comprising administering to the patient a therapeutically effective amount of a compound of Formula (I), or a pharmaceutically acceptable salt or solvate thereof, and at least one additional compound having hyperproliferative activity prior to, after, or simultaneously with the compound of Formula (I), or a pharmaceutically acceptable salt or solvate thereof, wherein the at least one of the additional compounds is selected from inhibitors of epidermal growth factor receptor (EGFR) tyrosine kinase, HER1 tyrosine kinase, or HER2 tyrosine kinase.

In another aspect the present disclosure provides use of a compound of Formula (I) according to any embodiments defined above for manufacture of a medicament for the treatment of a hyperproliferative disease or disorder.

Other aspects of the present disclosure may include suitable combinations of embodiments disclosed herein.

Hydrogen naturally occurs as a mixture of the isotopes $^1$H (hydrogen or protium), D ($^2$H or deuterium), and T ($^3$H or tritium). Deuterium (D or $^2$H) is a stable, non-radioactive isotope of hydrogen, with an atomic weight of 2.0144. The concentration of naturally abundant stable hydrogen isotopes is small and immaterial with respect to the degree of stable isotopic substitution of compounds of this invention. (Wada, E. & Hanba, Y., *Seikagaku,* 1994, 66(1):15-29; Ganes (Gannes), L. Z. et al., *Comp. Biochem. Physiol. A Mol Integr Physiol.*, 1998, 119(3):725-37.) In all chemical compounds with an H atom, the H atom actually represents a mixture of H and D, with about 0.015% being D. Thus, compounds with a level of deuterium greater than its natural abundance of 0.015% will be considered as unnatural and novel over their natural counterparts.

When a particular position is designated as having deuterium, it is understood that the abundance of deuterium at that position is at least 3400 fold higher than the natural abundance of deuterium (51% deuterium incorporation in the derivative as compared to 0.015% in natural compound).

The present invention in one aspect is based on the discovery that a therapeutic agent with certain hydrogen atoms replaced by deuterium atoms would possess enhanced stability while maintaining or improving therapeutic potency. Thus, one aspect of this invention is represented by combination of different biological active fragments and/or substitution of natural hydrogen with deuterium to create novel pharmaceutical agents for the treatment of hyperproliferative diseases or disorders, such as various cancers.

The description of the present disclosure herein should be construed in congruity with the laws and principals of chemical bonding. In some instances it may be necessary to remove a hydrogen atom in order to accommodate a substituent at any given location.

Thus, this disclosure is intended to cover all possible stereoisomers even when a single stereoisomer, or no stereochemistry, is described in a structure.

It should be understood that the compounds encompassed by the present disclosure are those that are suitably stable for use as pharmaceutical agents.

It is intended that the definition of any substituent or variable at a particular location in a molecule be independent of its definitions elsewhere in that molecule. For example, for substituent $(R^x)_n$, where n is 2, or two $R^x$ substituents at different positions of a structure, the two $R^x$ substituents are independent from each other, and each of the two $R^x$ groups may be the same or different.

In another set of embodiments, any atom not designated as deuterium in any of the embodiments of Formula (I) and Formulae (Ia) through (Ii) set forth above is present at its natural isotopic abundance.

Yet other aspects and embodiments may be found in the description provided herein.

Definitions

Definitions have been provided above for each of the groups defined. In addition, the following definitions shall be used.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions.

For example, the aryl part of an arylalkyl group such as benzyl may be substituted as described in the definition of the term "aryl."

The term "acetyl," as used herein, refers to —C(O)CH$_3$.

The term "alkenyl," as used herein, refers to a monovalent, straight or branched hydrocarbon chain having one or more, preferably one to two, double bonds therein. The double bond of an alkenyl group can be unconjugated or conjugated to another unsaturated group. Suitable alkenyl groups include, but are not limited to, C$_2$ to C$_{10}$ alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkoxy," as used herein, refers to an alkyl group attached to the parent molecular moiety through an oxygen atom. Representative examples of alkoxy group include, but are not limited to, methoxy (CH$_3$O—), ethoxy (CH$_3$CH$_2$O—), and t-butoxy ((CH$_3$)$_3$CO—).

The term "alkyl," as used herein, refers to a group derived from a straight or branched chain saturated hydrocarbon by removal of a hydrogen from one of the saturated carbons. The alkyl group preferably contains from one to ten carbon atoms. Representative examples of alkyl group include, but are not limited to, methyl, ethyl, isopropyl, and tert-butyl.

The term "alkylene," as used herein, refers to a divalent saturated hydrocarbon group derived by removal of two hydrogen atoms from a saturated hydrocarbon molecule. Representative examples of alkylene include, but are not limited to, methylene (—CH$_2$—), ethylene (—CH$_2$CH$_2$—), and n-propylene (—CH$_2$CH$_2$CH$_2$—). An "alkylene" group can be either straight- or branched-chain. For example, a "C$_4$ alkylene" includes, but is not limited to, —CH$_2$CH$_2$CH$_2$CH$_2$—, —CH$_2$CH(CH$_3$)CH$_2$—, and —CH$_2$CH$_2$CH(CH$_3$)—.

The term "aryl," as used herein, refers to a group derived from an aromatic carbocycle by removal of a hydrogen atom from an aromatic ring. The aryl group can be monocyclic, bicyclic or polycyclic, wherein in bicyclic or polycyclic aryl group, the aromatic carbocycle can be fused onto another four- to six-membered aromatic or non-aromatic carbocycle. Representative examples of aryl groups include, but are not limited to, phenyl, indanyl, indenyl, naphthyl, and 1,2,3,4-tetrahydronaphth-5-yl.

The term "benzyl," as used herein, refers to a methyl group on which one of the hydrogen atoms is replaced by a phenyl group, wherein said phenyl group may be substituted by one or more substituents. Representative examples of benzyl group include, but are not limited to, PhCH$_2$—, 4-MeO—C$_6$H$_4$CH$_2$—, and 2,4,6-tri-methyl-C$_6$H$_4$CH$_2$—.

The term "carbonyl," as used herein, refers to —C(O)—.

The term "carbocycle," as used herein, refers to a ring structure comprising only carbon atom in the ring. A carbocycle may optionally be fused onto another carbocyclyl, cycloalkyl, heterocyclyl, aryl, or heteroaryl ring structure.

The term "carbocyclyl," as used herein, refers to a group derived from a monocyclic, bicyclic, or polycyclic non-aromatic compound comprising a carbocycle by removal of one of the hydrogen atoms from the carbocycle ring. A carbocyclyl group is connected to the remaining molecular moiety through either a saturated or an unsaturated carbon. A carbocyclyl group may optionally be fused onto an aryl, heteroaryl, heterocyclyl or cycloalkyl ring.

The term "carboxyl," as used herein, refers to —CO$_2$H.

The term "cyano," as used herein, refers to —CN.

The term "cycloalkyl," as used herein, refers to a group derived from a monocyclic, bicyclic, or polycyclic saturated carbocycle, having preferably three to eight carbon atoms, by removal of a hydrogen atom from the saturated carbocycle, wherein the saturated carbocycle can optionally be fused onto one or two other aromatic or nonaromatic carbocycles. Representative examples of cycloalkyl groups include, but are not limited to, cyclopropyl, cyclopentyl, cyclohexyl, and 1,2,3,4-tetrahydronaphth-1-yl.

The term "formyl," as used herein, refers to —CHO.

The term "fused cycloalkyl," as used herein, refers to a cycloalkyl ring fused onto another ring structure, e.g., a saturated or unsaturated ring, including, for example, aryl, heteroaryl, heterocyclyl, or another cycloalkyl group. A cycloalkyl group, when referred to a bicyclic or polycyclic group, refers to such a group which attaches to the main molecular moiety through a carbon atom of a carbocycle of the group.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by at least one halogen atom. The haloalkyl group can be an alkyl group of which all hydrogen atoms are substituted by halogens. Representative examples of haloalkyl include, but are not limited to, trifluoromethyl (CF$_3$—), 1-chloroethyl (ClCH$_2$CH$_2$—), and 2,2,2-trifluoroethyl (CF$_3$CH$_2$—).

The term "heteroaryl," as used herein, refers to a group derived from a monocyclic, bicyclic, or polycyclic compound comprising at least one aromatic ring comprising one or more, preferably one to three, heteroatoms independently selected from nitrogen, oxygen, and sulfur, by removal of a hydrogen atom from the aromatic ring. As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, isoxazolyl, oxazolyl, indolyl, quinolinyl, isoquinolinyl, benzisoxazolyl, benzothiazolyl, benzothienyl, and pyrrolopyridinyl.

The term "heterocyclyl," as used herein, refers to a group derived from a monocyclic, bicyclic, or polycyclic compound comprising at least one nonaromatic ring comprising one or more, preferably one to three, heteroatoms independently selected from nitrogen, oxygen, and sulfur, by removal of a hydrogen atom from the nonaromatic ring. The heterocyclyl groups of the present disclosure can be attached to the parent molecular moiety through a carbon atom or a nitrogen atom in the group. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl.

The terms "hydroxy" or "hydroxyl," as used herein, refer to —OH.

The term "nitro," as used herein, refers to —NO$_2$.

The term "—NR$^a$R$^b$," as used herein, refers to two groups, R$^a$ and R$^b$, which are attached to the parent molecular moiety through a nitrogen atom, or alternatively R$^a$ and R$^b$, together with the nitrogen atom to which they are attached, form a 5- or 6-membered ring or a fused- or bridged-bicyclic ring structure optionally containing one, two, or three additional heteroatom independently selected from nitrogen, oxygen, and sulfur. The term "—NR$^c$R$^d$" is defined similarly.

The term "oxo," as used herein, refers to "=O".

The term "sulfonyl," as used herein, refers to "-SO$_2$-". For example, the term "alkylsulfonyl" refers to a group R-S(O)$_2$-, wherein R is alkyl; the term "aminosulfonyl" refers to a group -SO$_2$NH$_2$.

The term "sulfinyl," as used herein, refers to "—S(O)—". For example, the term "alkylsulfinyl," refers to a group R—S(O)$_2$—, wherein R is alkyl; the term "aminosulfinyl" refers to a —S(O)NH$_2$.

In another embodiment of this invention, the compounds of the present invention contain one or more stereogenic centers. As such, a compound of this invention can exist as the individual stereoisomers (enantiomers or diastereomers) as well as a mixture of stereoisomers.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof. Individual stereoisomers of compounds can be prepared synthetically from commercially available starting materials, which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms that may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, or mixtures and salts thereof. Similarly, references to intermediates are meant to embrace their salts where the context so permits.

The compounds of the present disclosure can exist as pharmaceutically acceptable salts or solvates. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

In another embodiment of this invention, a salt of the compounds of this invention is formed between an acid and a basic group of the compound, such as an amino functional group, or a base and an acidic group of the compound, even such as an amide group. The "pharmaceutically acceptable salts," as used in this invention, refers to a component which is, within the scope of medical judgment, suitable for use with tissues of humans and other mammals without undesired toxicity, irritation, allergic response or are commensurate with a reasonable benefit/risk ratio. A "pharmaceutically acceptable salt" means any non-toxic salt that, upon administration to a recipient, is capable of providing the compounds or the prodrugs of a compound of this invention.

Acids commonly employed to form pharmaceutically acceptable salts include inorganic acids such as hydrochloric acid, hydrobromic acid, hydroiodic acid, sulfuric acid, phosphoric acid, hydrogen bisulfide as well as organic acids, such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, acetic acid, and related inorganic and organic acids.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, triethanolamine, piperidine, piperazine, 1H-imidazole, choline, N-methylglucamine, lysine, arginine, benethamine, benzathine, betaine, decanol, 2-(diethylamini)ethanol, hydrabamine, 4-(2-hydroxyethyl)morpholine, 1-(2-hydroxyethyl)pyrrolidine, and tromethamine.

The term "prodrug," as used herein, refers to compounds that are transformed in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

When it is possible that, for use in therapy, therapeutically effective amounts of a compound of Formula (I), as well as pharmaceutically acceptable salts or solvates thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts or solvates thereof, and one or more, preferably one to three, pharmaceutically acceptable carriers, diluents, or excipients.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Synthetic Methods

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

Preferred methods include, but are not limited to, those described, for instance, in U.S. Pat. No. 5,747,498, EP 1,110,953, EP 817,775, U.S. Pat. No. 6,900,221, U.S. Pat. No. 6,476,040 and PCT publications WO2009/094210, WO2009/121042 and WO2009/094216. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Common abbreviations listed below may be used in this disclosure.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
$CH_2Cl_2$ dichloromethane
$CH_3CN$ or ACN acetonitrile
$CDCl_3$ deutero-chloroform
$CHCl_3$ chloroform
DCM dichloromethane
DEAD diethyl azodicarboxylate
DIPEA or $iPr_2EtN$ diisopropylethylamine
DMF dimethyl formamide
DMSO dimethyl sulfoxide
EDC or EDAC N-(3-dimethylaminopropyl)-N'-ethylcarbodiimide
$Et_3N$ or TEA triethylamine
EtOAc ethyl acetate
$Et_2O$ diethyl ether
EtOH ethanol
HCl hydrochloric acid
HOBt 1-hydroxybenzotriazole
$HNO_3$ nitric acid
$H_2SO_4$ sulfuric acid
$K_2CO_3$ potassium carbonate
KOAc potassium acetate
$K_3PO_4$ potassium phosphate
LiOH lithium hydroxide
MeOH methanol
$MgSO_4$ magnesium sulfate
MsOH or MSA methylsulfonic acid
NaCl sodium chloride
$Na(OAc)_3BH$ sodium triacetate borohydride
$NaHCO_3$ sodium bicarbonate
$Na_2CO_3$ sodium carbonate
NaOH sodium hydroxide
NaOMe sodium methoxide
$Na_2SO_4$ sodium sulfate
$NH_3$ ammonia
$NH_4Cl$ ammonium chloride
$NH_4OH$ ammonium hydroxide
$Pd(OAc)_2$ palladium(II) acetate
Pd/C palladium on carbon
$PPh_3$ triphenylphosphine POCl₃ phosphorus oxychloride
PtO₂ platinum oxide
i-PrOH or IPA isopropanol
TFA trifluoroacetic acid
THF tetrahydrofuran A convenient method for synthesizing part of compounds of Formula (Ia)-1 is depicted in Scheme 1 above. Reaction of compound 1, which is commercially available, with 1-chloro-2-d₃-methoxyethane in the presence of potassium carbonate in acetone with catalyst of tert-butyl ammonium chloride provides 2. Nitration of 2 with nitric acid in acetic acid gives 3 as product in very good yield. This reaction has been published in the literature, e.g., Knesl, *Molecules*, 2006, 11, 286. The intermediate 3 then is reduced to amino derivatives by hydrogen with catalyst of platinum and consequently cyclized with formamide in 160-170° C. to give product 5. The amide is converted to chloride with POCl₃ to give compound 6, and 6 can be coupled with different aniline derivatives 7 to finish the synthesis of (Ia)-1.

The synthesis of 1-chloro-2-d₃-methoxyethane is depicted in Scheme 2 below. Starting with commercial compound 1-chloro-2-bromoethane, the 1-chloro-2-d₃-methoxyethane can be synthesized with deuterated methanol with potassium carbonate. For those compounds containing N-deuterated 7, they can be easily synthesized by catalytic hydrogenation of nitro precursors with D₂ or coupling of commercial ND₃OD in DMF as depicted in latest literature. (Ning Xia, *Angew. Chem. Int. Ed.*, 2009, 48, 337).

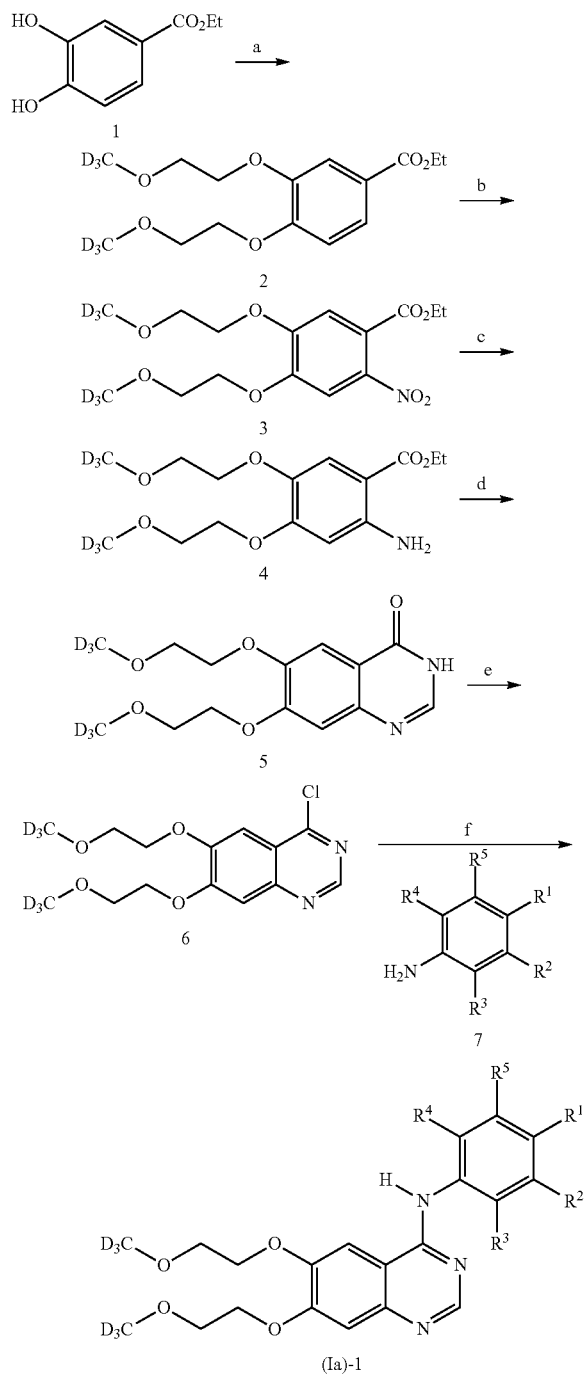

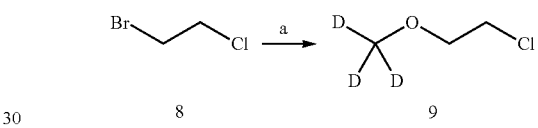

Scheme 2. Synthesis of 1-chloro-2-D₃-methoxyethane a) MeOH-d₄, K₂CO₃, N,N-dimethyl formamide.

A convenient method for the synthesis of compounds of Formula (Ib)-1 is depicted in Scheme 3. Reaction of 10 (synthesized according to Harris, *Tetrahedron Lett.*, 2005, 46, 1835) with R⁷I in the presence of potassium carbonate in DMF to give compounds 11. 11 are demethylated with acid to provide compounds 12. After acetylation of 12, compounds 13 are converted to chloro compounds 14 using phosphorous chloride in the presence of an amine base. Removal of the acetyl group from 14 provides phenols 15, which is subsequently coupled with alcohols or deuterated alcohols under Mitsunobu conditions to obtain compounds 16. Coupling of 16 with anilines or N-deuterated anilines 17 in DMF with potassium carbonate then provide the compounds of formula (Ib)-1 as shown.

a) 1-chloro-2-d₃-methoxyethane, K₂CO₃, Bu₄N⁺Br⁻, acetone; b) AcOH, HNO₃, 0-5° C.; c) PtO₂•H₂O, H₂; d) formamide, 165-170° C.; e) POCl₃, N,N-diethylaniline; f) compound 7; g) i-PrOH, reflux.

Scheme 3. Synthesis of Compounds of Formula (Ib)-1

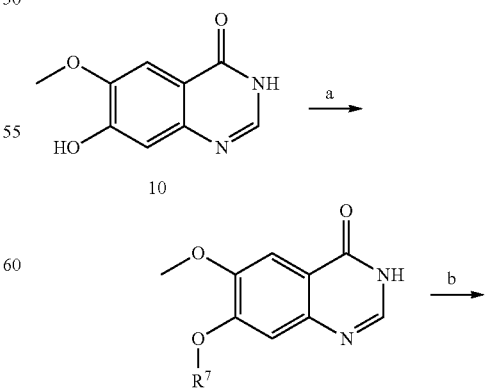

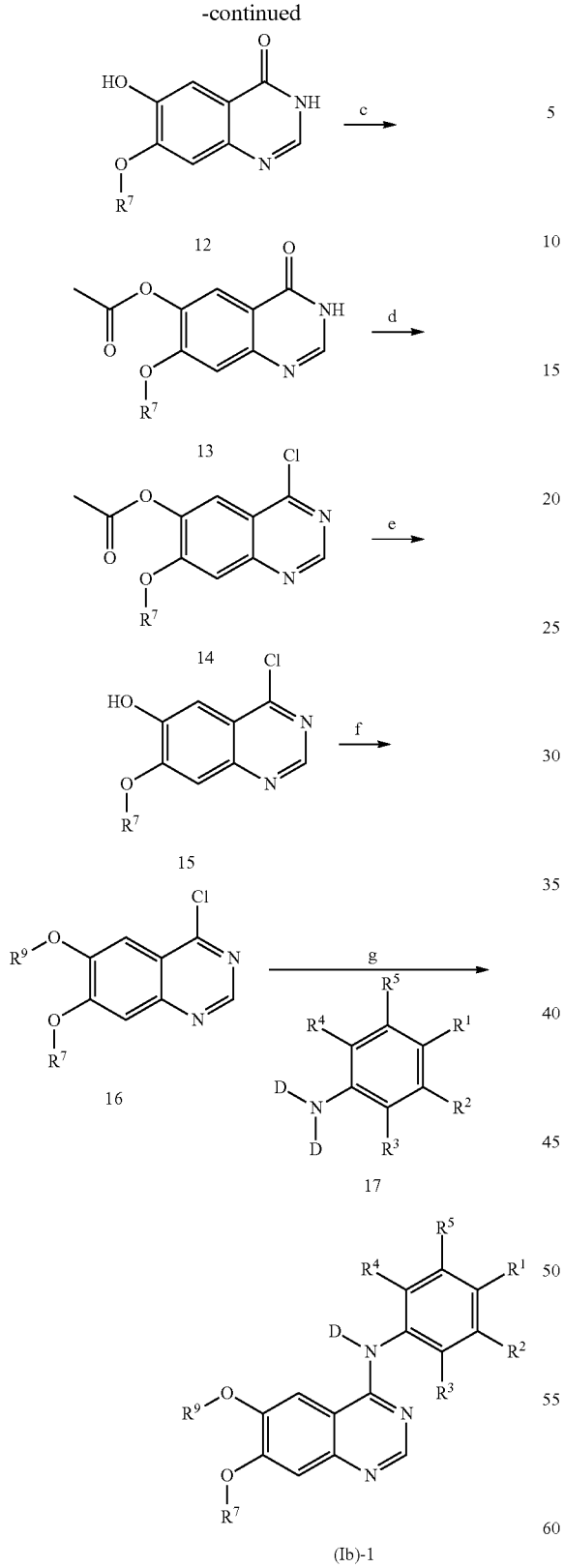

a) R⁷I, K₂CO₃, DMF; b) MeSO₃H, L-Methionine; c) Ac₂O, Pyr., 100° C.; d) POCl₃, N,N-diethylaniline; e) 10% NH₃/MeOH, 80° C.; f) R⁹OH, PPh₃, DEAD; g) compound 17, i-PrOH, reflux.

A convenient method for the synthesis of compounds of Formula (Ih)-1 is depicted in Scheme 4. Reaction of commercially available (e.g., from Sigma-Aldrich) 18 with N,N-deuterated anilines, which can be practically synthesized as depicted above, gives compounds 19 using iso-propanol as solvent. 19 are coupled with 5-formylfuran-2-ylboric acid under Suzuki coupling condition to obtain 20 in very good yields (Kimberly G. Petrov, *Bioorg. Med. Chem. Lett.*, 2006, 16, 4686). Then the aldehydes are reduced to secondary amines 21, and the tertial amines (Ih)-1 can be easily synthesized by coupling 21 with different halogen containing compounds.

Scheme 4. Synthesis of Compounds of Formula (Ih)-1

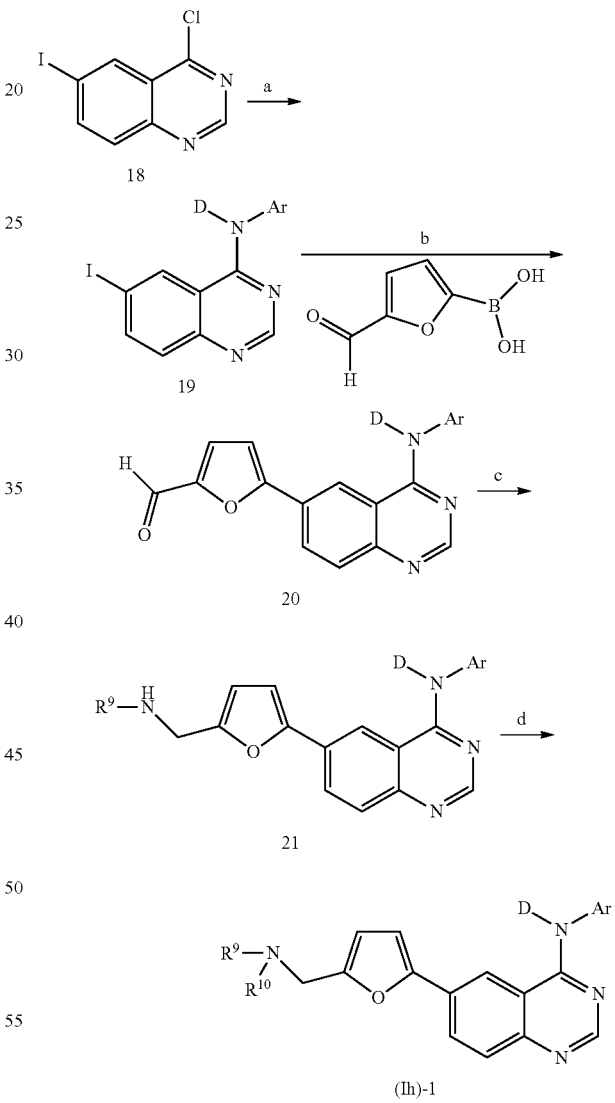

a) ArNH₂, IPA, 70° C.; b) 5-formylfuran-2-ylboric acid, Pd(OAc)₂, PPh₃, Et₃N, DMF; c) R⁹NH₂, Na(OAc)₃BH; d) R¹⁰X, iPr₂EtN, DMF.

The convenient method for the synthesis of compounds of Formula (If)-1 is depicted in Scheme 5. The starting material 24 is commercially available from most of vendors (e.g. Aldrich), and can be selectively nitrated in position 4 to give 25. (Gordon Rewcastle, *J. Med. Chem.*, 1996, 39, 918). Then amide 25 is converted into chloro compound 27 and coupled with aniline or deuterated aniline derivatives in IPA to yield 28. The fluoro group in 28 is substituted by R⁷OH under basic condition to obtain 29 in good yields. Finally, the nitro groups in 29 are reduced and the anilines 30 subsequently couple with acrylic acid derivatives 26 to give final compounds (If)-1 as solids.

Scheme 5. Synthesis of Compounds of Formula (If)-1

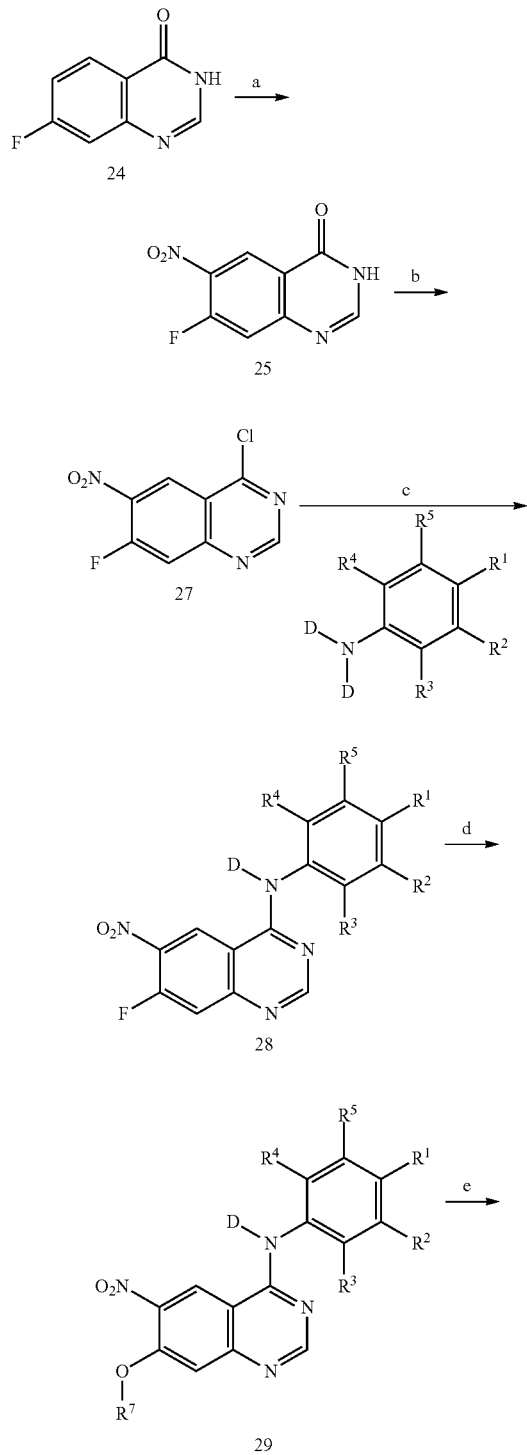

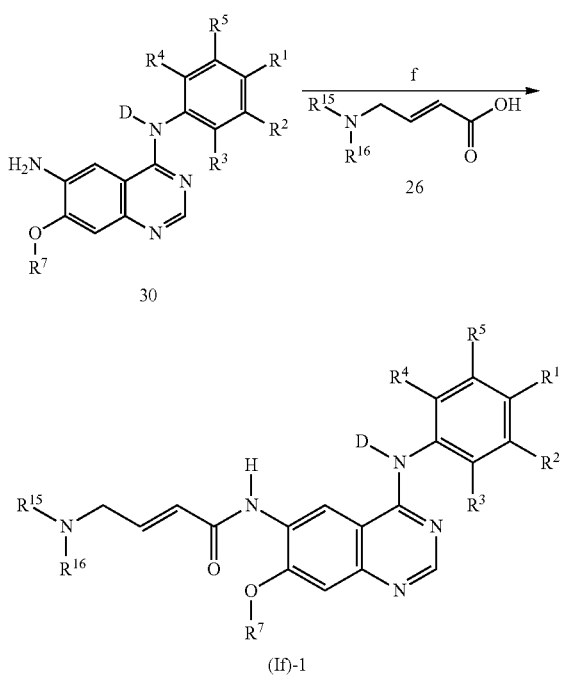

a) c. H₂SO₄, f. HNO₃, 100° C., b) POCl₃, N,N-diethylaniline, c) 17, IPA, reflux, d) R⁷OH, NaOMe, DMSO, e) Pd/C, H₂, f) 26, EDAC, HOBt, DMF

EXAMPLES

Certain preferred embodiments of the present invention are illustratively shown in the following non-limiting examples.

Example 1

(S,E)-N-(4-(3-chloro-4-fluorophenylamino)-7-(tetrahydrofuran-3-yloxy)quinazolin-6-yl)-4-(D₆-dimethylamino)but-2-enamide

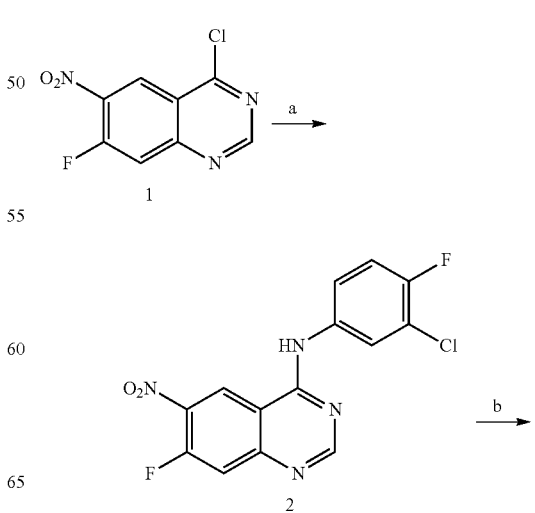

-continued

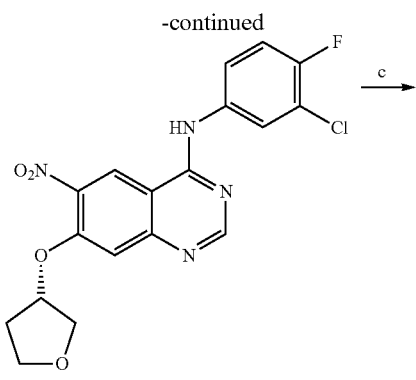

3

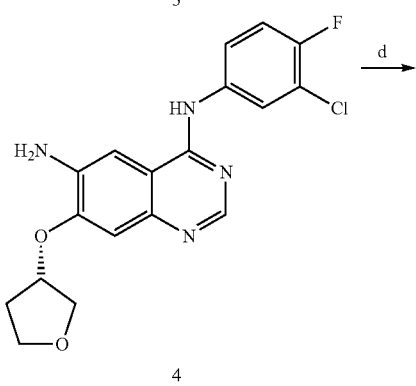

4

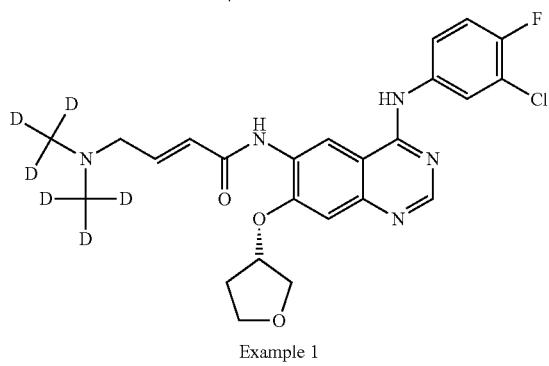

Example 1

N-(3-chloro-4-fluorophenyl)-7-fluoro-6-nitro-quinazolin-4-amine (2)

230 mg of 1 (1.0 mmol) and 146 mg 3-chloro-4-fluoroaniline (1.0 equivalent) were suspended in 5 ml isopropanol and heated to reflux for 4 h. The mixture was cooled to room temperature and solvent was evaporated under vacuum to give crude product. The crude product was dissolved in dichlormethane and basified by 10% NaOH solution. The organic layer was separated and dried to give pure product 2 as yellow solid. yield 100%. HPLC-MS: m/z: 337 [M+1]$^+$.

(S)—N-(3-chloro-4-fluorophenyl)-6-nitro-7-(tetrahydrafuran-3-yloxy)quinazolin-4-amine (3)

200 mg of 2 (0.6 mmol) was dissolved in 5 ml DMF and potassium trimethylsilanolate 115 mg 9 (0.9 mmol) was added and stirred for 15 min at room temperature. Then, (s)-tetrahydrafuran-3-ol 0.72 mmol was dropped in under stirring and the mixture was stirred over night. The solvent was concentrated and the product was purified by column chromatography to yield product 3 as yellow solid, 200 mg, 85% yield. HPLC-MS: m/z: 405 [M+1]$^+$.

(S)—N-(3-chloro-4-fluorophenyl)-6-amino-7-(tetrahydrafuran-3-yloxy)quinazolin-4-amine (4)

The purified 3 200 mg was dissolved in 6 ml acetic acid, 2 ml water, 0.6 ml conc. HCl solution and 200 mg iron powder, and heated to reflux for 4 h. The solvents were evaporated and residue was dissolved in dichloromethane and basified by 10% NaOH. The organic layer was dried and concentrated. The product was purified by column chromatography to yield 160 mg product 4 as brown solid. HPLC-MS: m/z: 375 [M+1]$^+$.

(S,E)—N-(4-(3-chloro-4-fluorophenylamino)-7-(tetrahydrafuran-3-yloxy)quinazolin-6-yl)-4-($D_6$-dimethylamino)but-2-enamide (Example 1)

110 mg of 4-($D_6$-dimethyl)amino-2-butenoic acid (0.63 mmol) which was prepared by reaction between 4-bromo-2-butenoic acid and dimethylamine-$d_6$ gas in THF, was added in 2 ml DMF and 200 mg of 4 (0.53 mmol) was added followed by 0.6 mmol EDC. The mixture was stirred over night at room temperature and the final product was purified by preparative HPLC to give 125 mg product as light yellow solid, yield 40%. HPLC-MS: m/z: 492 [M+1]$^+$.

Example 2

(S,E)-4-($D_6$-dimethylamino)-N-(4-(3-ethynylphenylamino)-7-(tetrahydrofuran-3-yloxy)quinazolin-6-yl)but-2-enamide

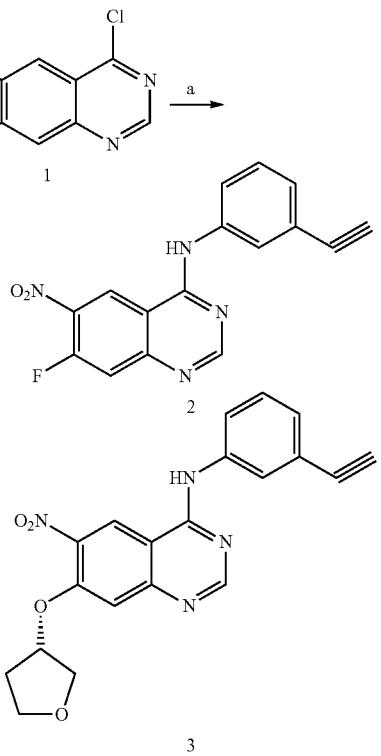

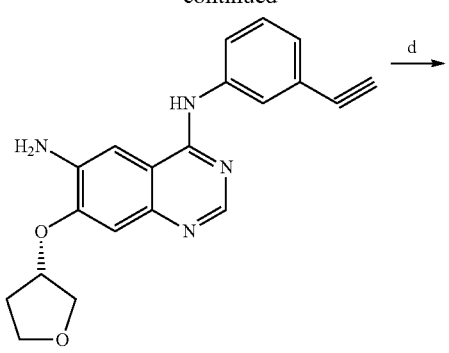

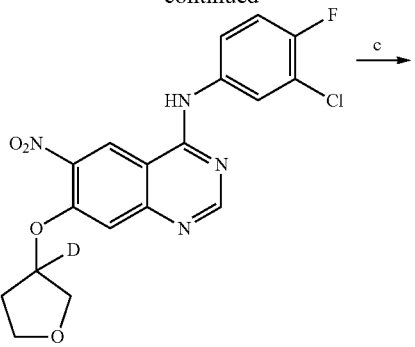

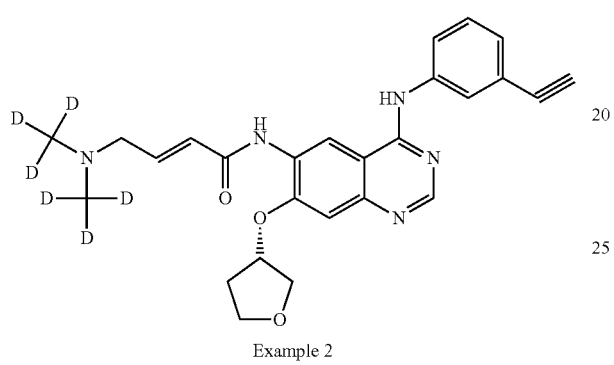

Example 2

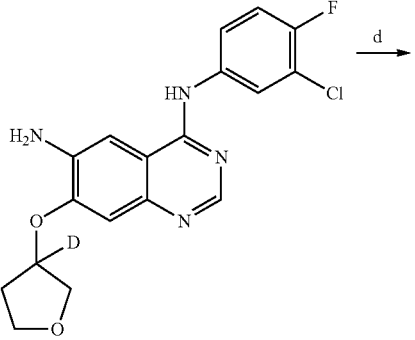

As depicted in above scheme, this compound was synthesized similar as (S,E)-N-(4-(3-chloro-4-fluorophenylamino)-7-(tetrahydrafuran-3-yloxy)quinazolin-6-yl)-4-(D$_6$-dimethylamino)but-2-enamide by using 3-ethynylaniline in place of 3-chloro-4-fluoroaniline The final product was purified by HPLC to yield 50 mg of product as white solid. HPLC-MS: m/z: 464 [M+1]+.

Example 3

(E)-N-(4-(3-chloro-4-fluorophenylamino)-7-((3-D)-tetrahydrofuran-3-yloxy)quinazolin-6-yl)-4-(dimethylamino)but-2-enamide

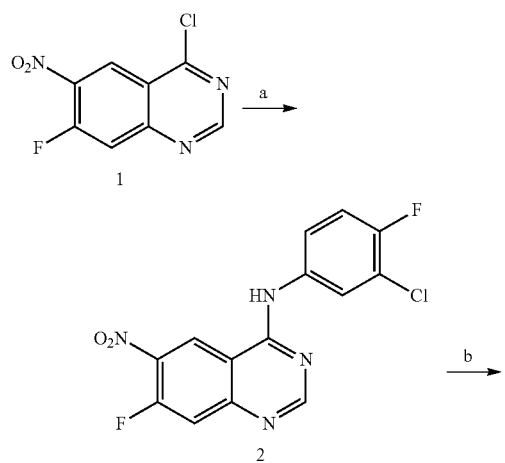

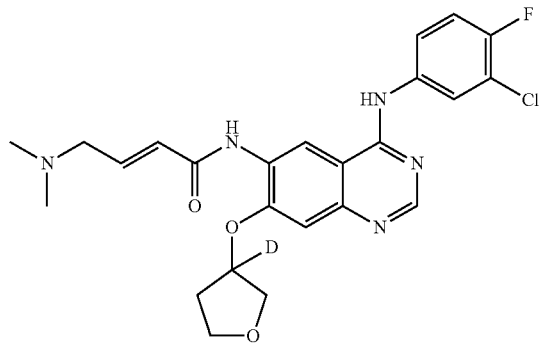

Example 3

N-(3-chloro-4-fluorophenyl)-7-fluoro-6-nitro-quinazolin-4-amine (2)

230 mg of 1 (1.0 mmol) and 146 mg 3-chloro-4-fluoroaniline (1.0 equivalent) were suspended in 5 ml isopropanol and heated to reflux for 4 h. The mixture was cooled to room temperature and solvent was evaporated under vacuum to give crude product. The crude product was dissolved in dichlormethane and basified by 10% NaOH solution. The organic layer was separated and dried to give pure product 2 as yellow solid. yield 100%. HPLC-MS: m/z: 337 [M+1]+.

N-(3-chloro-4-fluorophenyl)-6-nitro-7-(3-D-tetrahydrafuran-3-yloxy)quinazolin-4-amine (3)

200 mg of 2 (0.6 mmol) was dissolved in 5 ml DMF and potassium trimethylsilanolate 115 mg 9 (0.9 mmol) was added and stirred for 15 min at room temperature. Then, 0.72 mmol of 3-D-tetrahydrafuran-3-ol, which was prepared by reduction of dihydrofuran-3(2H)-one with LiAlD$_4$, was dropped in under stirring and the mixture was stirred over night. The solvent was concentrated and the product was purified by column chromatography to yield product 3 as yellow solid, 205 mg, 85% yield. HPLC-MS: m/z: 406 [M+1]$^+$.

N-(3-chloro-4-fluorophenyl)-6-amino-7-(3-D-tetrahydrafuran-3-yloxy)quinazolin-4-amine (4)

The purified 3 200 mg was dissolved in 6 ml acetic acid, 2 ml water and 0.6 ml conc. HCl solution and heated to reflux for 4 h. The solvents were evaporated and residue was dissolved in dichloromethane and basified by 10% NaOH. The organic layer was dried and concentrated. The product was purified by column chromatography to yield 150 mg product 4 as brown solid. HPLC-MS: m/z: 375 [M+1]$^+$.

N-(4-(3-chloro-4-fluorophenylamino)-7-(3-D-tetrahydrafuran-3-yloxy)quinazolin-6-yl)-4-(dimethylamino)but-2-enamide (Example 3)

100 mg of 4-dimethylamino-2-butenoic acid (0.63 mmol) which was prepared by reaction between 4-bromo-2-butenoic acid and dimethylamine in THF, was added in 2 ml DMF and 185 mg of 4 (0.53 mmol) was added followed by 0.6 mmol EDC. The mixture was stirred over night at room temperature and the final product was purified by preparative HPLC to give 120 mg product as light yellow solid, yield 40%. HPLC-MS: m/z: 496 [M+1]$^+$.

Example 4

(E)-4-(dimethylamino)-N-(4-(3-ethynylphenylamino)-7-(3-D-tetrahydrofuran-3-yloxy)quinazolin-6-yl)but-2-enamide As depicted in scheme below, this compound was synthesized similar as N-(4-(3-chloro-4-fluorophenylamino)-7-(1-D-tetrahydrafuran-3-yloxy)quinazolin-6-yl)-4-(dimethylamino)-but-2-enamide by using 3-ethynylaniline in place of 3-chloro-4-fluoroaniline. The final product was purified by HPLC to yield 40 mg of product as light yellow solid. HPLC-MS: m/z: 459 [M+1]$^+$.

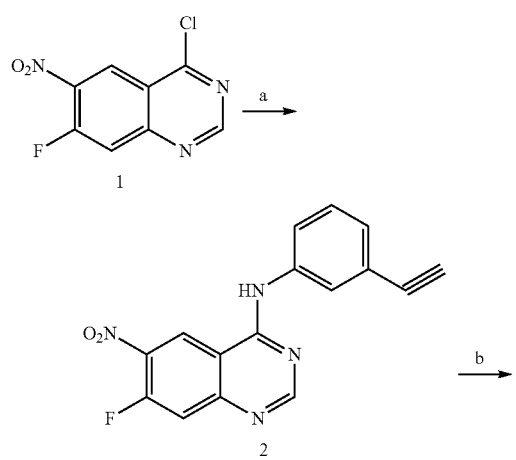

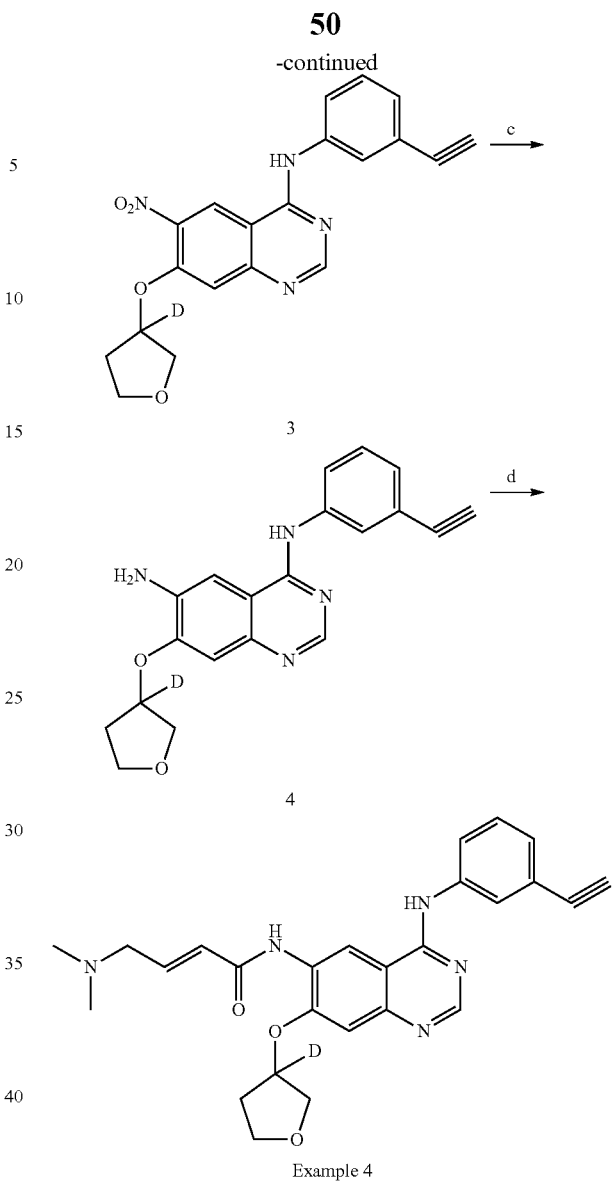

Example 4

Example 5

7-(4-(3-ethynylphenylamino)-7-(D$_3$-methoxy)quinazolin-6-yloxy)-N-hydroxyheptanamide This compound was synthesized by the following steps according to the scheme below.

Ethyl 3-hydroxy-4-(D$_3$-methoxy)benzoate (2)

Potassium carbonate (3.8 g, 27.5 mmol) was added to a stirred solution of 1 (5.0 g, 27.5 mmol) in DMF (20 mL). After the mixture was stirred at room temperature for 15 min, a solution of iodomethane-d3 (4.1 g, 27.5 mmol) in DMF (4 mL) was added dropwise. The reaction mixture was stirred at 20° C. for 24 h. The mixture was filtered and the filtrate was concentrated. The residue was dissolved in dichloromethane and washed with brine. The organic phase was dried over sodium sulfate, filtered and concentrated in vacuo to give the crude product which was purified by column chromatography (silica gel, 1:10 ethyl acetate/petroleum ether) to yield 2 as a white solid (2.8 g, 50%). HPLC-MS: m/z 201 [M+H]+.

Ethyl 3-(7-ethoxy-7-oxoheptyloxy)-4-(D₃-methoxy) benzoate (3)

A mixture of compound 2 (6.5 g, 32.3 mmol), ethyl 7-bromoheptanoate (7.66 g, 32.3 mmol) and potassium carbonate (13.38 g, 96.9 mmol) in DMF (80 mL) was stirred at 60° C. for 3 h. The reaction mixture was filtered and the filtrate was concentrated in vacuo. The residue was dissolved in dichloromethane and washed with brine. The organic phase was dried over sodium sulfate, filtered and concentrated to give 3 as a white solid (10 g, 85%). LCMS: m/z 356 [M+H]+.

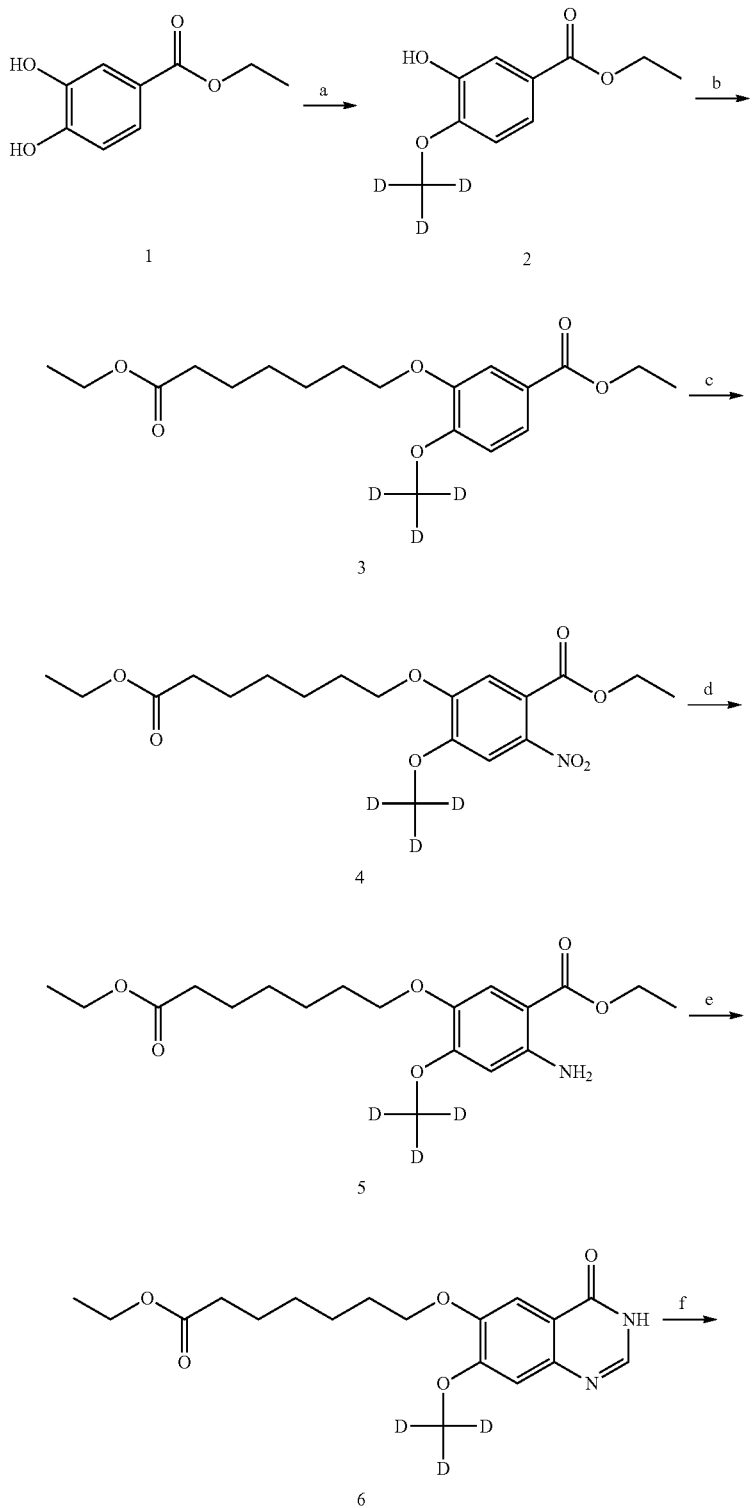

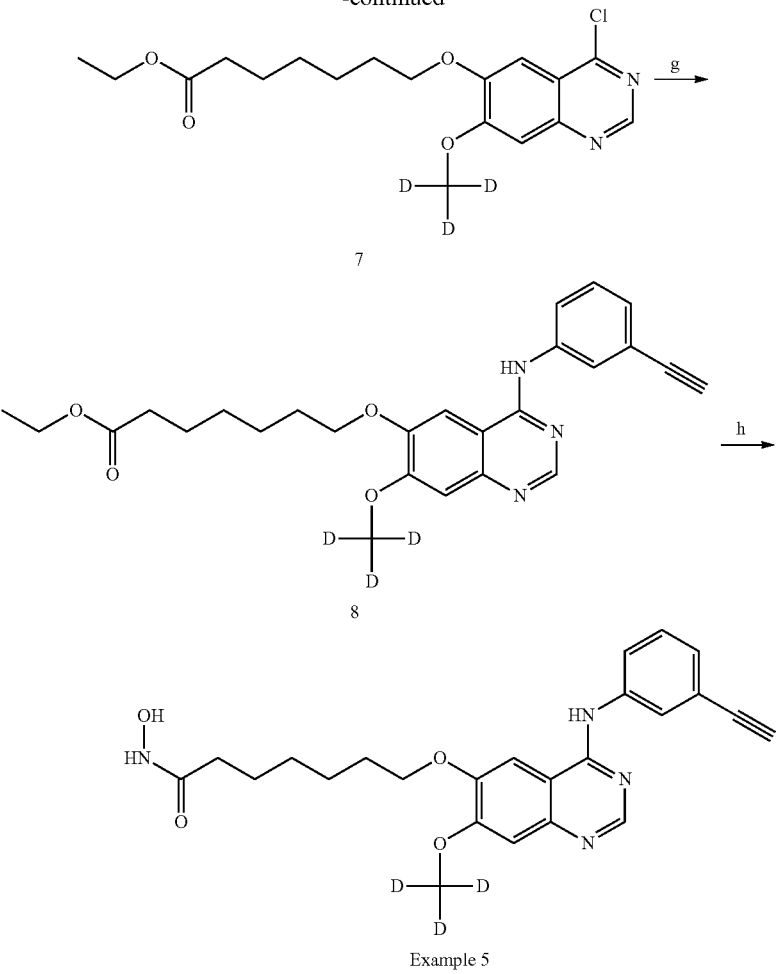

Example 5

Ethyl 5-(7-ethoxy-7-oxoheptyloxy)-4-(D₃-methoxy)-2-nitrobenzoate (4)

10 equivalent of fuming nitric acid was added dropwise at 20° C. to a solution of 3 (0.82 g, 2.3 mmol) in acetic acid (3 mL). The mixture was stirred at 20° C. for additional 1 h. The mixture was poured into ice-water and extracted with dichloromethane. The organic layer was washed with water, aqueous NaHCO3 and brine, dried over sodium sulfate, filtered, and evaporated in vacuo to give 4 as a yellow solid (0.92 g, 100%). HPLC-MS (ESI): m/z 401 [M+H]⁺.

Ethyl 2-amino-5-(7-ethoxy-7-oxoheptyloxy)-4-(D₃-methoxy)benzoate (5)

Iron powder (40.0 mmol) was added portionwise to a solution of 4 (0.9 g 2.0 mmol) in the mixed solvents of ethanol (3 mL), water (1 mL) and conc. hydrochloric acid (0.1 mL). The mixture was stirred at reflux for 30 min. The mixture was then cooled to room temperature and adjusted to pH8 with the addition of 10% sodium hydroxide solution. The resultant precipitate was removed by filtration and the filtrate was concentrated. The residue was extracted with dichloromethane. The extract was washed with brine, dried over sodium sulfate, filtered and concentrated to give 5 as a yellow solid (0.7 g, 88%). HPLC-MS: m/z 371 [M+H]⁺.

Ethyl 7-(7-(D₃-methoxy)-4-oxo-3,4-dihydroquinazolin-6-yloxy)heptanoate (6)

A mixture of 5 (0.3 g, 0.81 mmol), ammonium formate 1.0 equivalent and formamide (2 mL) was stirred at 180° C. for 3 h. The mixture was cooled to room temperature and the excess formamide was removed in vacuo. The residue was dissolved in dichloromethane, and washed with water and brine. The organic layer was dried over sodium sulfate, filtered, and concentrated to give 6 as a pale yellow solid (0.28 g, 99%). HPLC-MS (ESI): m/z 352 [M+H]⁺.

Ethyl 7-(4-chloro-7-(D₃-methoxy)quinazolin-6-yloxy)heptanoate (7)

A mixture of 6 (0.12 g, 0.34 mmol) and phosphoryl trichloride (2 mL) was stirred at reflux for 4 h. The reaction mixture was then cooled to room temperature and the excess phosphoryl trichloride was removed in vacuo. The residue was dissolved in dichloromethane and washed with water, aqueous NaHCO3, and brine. The organic layer was then dried over sodium sulfate, filtered, and concentrated to give the 7 as a yellow oil, which turned to solid while standing (0.11 g, 80%). HPLC-MS: m/z 370 [M+H]⁺.

Ethyl 7-(4-(3-ethynylphenylamino)-7-($D_3$-methoxy) quinazolin-6-yloxy)heptanoate (8)

A mixture of 7 (37 mg, 0.1 mmol) and 3-ethynylbenzenamine (117 mg, 0.1 mmol) in isopropanol (5 mL) was stirred at reflux for 4 h. The reaction was allowed to cool to room temperature and the precipitate formed. The precipitate was collected by filtration, washed with isopropanol and ether, and dried to give 8 as a yellow solid (40 mg, 80%). HPLC-MS (ESI): m/z 451 [M+H]$^+$.

7-(4-(3-ethynylphenylamino)-7-($D_3$-methoxy) quinazolin-6-yloxy)-N-hydroxyheptanamide (Example 5)

The ester 8 (1.0 mmol) were added to the freshly prepared hydroxylamine solution (3 mL) at 0° C. The reaction mixture was warmed to room temperature and stirred at 25° C. for 8 h until the reaction was complete. The reaction mixture was neutralized with acetic acid. The formed precipitate was collected by filtration, washed with water, and dried. The final product was purified by column chromatography to give pure product as light yellow solid (400 mg, 85%). HPLC-MS: m/z 438 [M+H]$^+$.

Other non-limiting examples embodied in this application can be similarly synthesized by a person of ordinary skill in the art using the methods described above and routine knowledge or techniques commonly used in the organic chemistry field.

Evaluation of Compound Stability in Human Liver Microsomes

The liver microsomes stability of compounds of Examples 1-4 was compared with that of TOVOK, and the compound of Example 5 with CUDC-101.
Assay System:
The metabolic stability of compounds of the invention was tested using pooled liver microsomes prepared from mixed-gender humans, with 1 mM NADPH. The samples were analyzed using an LTQ-Orbitrap XL mass spectrometer. HRMS was used to determine the peak area response ratio (peak area corresponding to test compound or control divided by that of an analytical internal standard) without running a standard curve. HRMS scan was performed in an appropriate m/z range in order to detect all plausible metabolites
Assay Conditions
The assay was run with a single incubation (N=1). Incubated test compounds at 37° C. in buffer containing 0.5 mg/mL microsomal protein. Initiated the reaction by adding cofactors, sampling at 0, 10, 20, 30, and 60 minutes, Incubated positive control (5 µM testosterone) in parallel and sampling at 0, 10, and 30 minutes.
Assay QC
The control compound testosterone was run in parallel to verify the enzymatic activity of the microsomes. After the final time point, fluorimetry was used to confirm the addition of NADPH to the reaction mixture. $T_{1/2}$ of control met the internal acceptance criteria.
Analytical Method
Liquid Chromatography
Column: Thermo BDS Hypersil C18 30×2.0 mm, 3 µm, with guard column
M.P. Buffer: 25 mM ammonium formate buffer, pH 3.5
Aqueous Reservoir (A): 90% water, 10% buffer
Organic Reservoir (B): 90% acetonitrile, 10% buffer
Flow Rate: 300 µL/minute
Gradient Program:

| Time (Min) | % A | % B |
|---|---|---|
| 0.0 | 100 | 0 |
| 1.5 | 0 | 100 |
| 2.0 | 0 | 100 |
| 2.1 | 100 | 0 |
| 3.5 | 100 | 0 |

Total Run Time: 3.5 minutes
Autosampler: 10 µL Injection Volume
Autosampler Wash: water/methanol/2-propanol: 1/1/1; with 0.2% formic acid
Mass Spectrometer
Instrument: PE SCIEX API 3000
Interface: Turbo Ionspray
Mode: Multiple Reaction Monitoring
Method: 3.5 minute duration The results are shown in Table 1. Under the experiment conditions, all compounds as exampled in the table dramatically improve the human liver microsome stabilities. Therefore, they have the potentialities to lower medical dosage comparing the reference compounds.

TABLE 1

Stability in Human Liver Microsomes

| Test compounds | Percentage remaining | | | | | Half life (min) |
|---|---|---|---|---|---|---|
| | 0 min | 10 min | 20 min | 30 min | 60 min | |
| Example 1 | 100 | 97 | 90 | 85 | 75 | >60 |
| Example 2 | 100 | 95 | 87 | 80 | 67 | >60 |
| Example 3 | 100 | 97 | 89 | 84 | 73 | >60 |
| Example 4 | 100 | 94 | 87 | 79 | 70 | >60 |
| TOVOK | 100 | 95 | 85 | 75 | 60 | >60 |
| Example 5 | 100 | 85 | 68 | 48 | 25 | 28 |
| CUDC-101 | 100 | 74 | 48 | 35 | 14 | 20 |

The compounds of instant invention are useful for treatment of various cancers, including, but not limited to, non-small cell lung cancer, breast cancer, brain tumor, pancreas cancer, heptocellular carcinoma, colorectal cancer, medullary thyroid cancer, gliomas, neuroblastomas, kidney tumors, ovarian cancers, and prostate cancers.

The compounds disclosed in this invention can be used alone or in combination with other agents for the treatment of a variety of cancers, including, but not limited to lung cancer, pancreatic cancer, astrocytoma, renal cancer, head and neck cancer, breast cancer, bladder cancer, ovarian cancer, colorectal cancer, prostate cancer, cervical cancer, thymoma cancer, liver cancer, and gastric cancer.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

All patents, patent applications, and literature references cited in the specification are herein incorporated by reference in their entirety. In the case of inconsistencies, the present disclosure, including definitions, will prevail.

What is claimed is:

1. A compound of formula (If) or a pharmaceutically acceptable salt thereof:

(If)

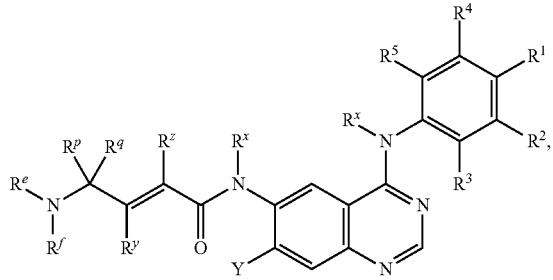

wherein $R^1$, $R^2$, $R^3$, $R^4$, and $R^5$ are each independently selected from the group consisting of hydrogen, deuterium, alkyl, alkenyl, alkynyl, cycloalkyl, aryl, heteroaryl, heterocyclyl, halogen, cyano, -L-$R^6$, —$OR^7$, —$C(O)OR^8$, —$OC(O)R^9$, —$C(O)R^{10}$, —$SR^{11}$, —$S(O)_2R^{12}$, —$S(O)R^{12}$, —$NR^aR^b$, and —$NHC(O)R^{13}$, wherein said alkyl, alkenyl, alkynyl, cycloalkyl, aryl, heteroaryl, and heterocyclyl each may optionally comprise one or more deuterium atoms;

Y is selected from the group consisting of from hydrogen, deuterium, —$OCH_3$, —$OCD_3$, —$OCD_2CH_3$, —$OCH_2CD_2OCH_3$, —$OCH_2CH_2OCD_3$,

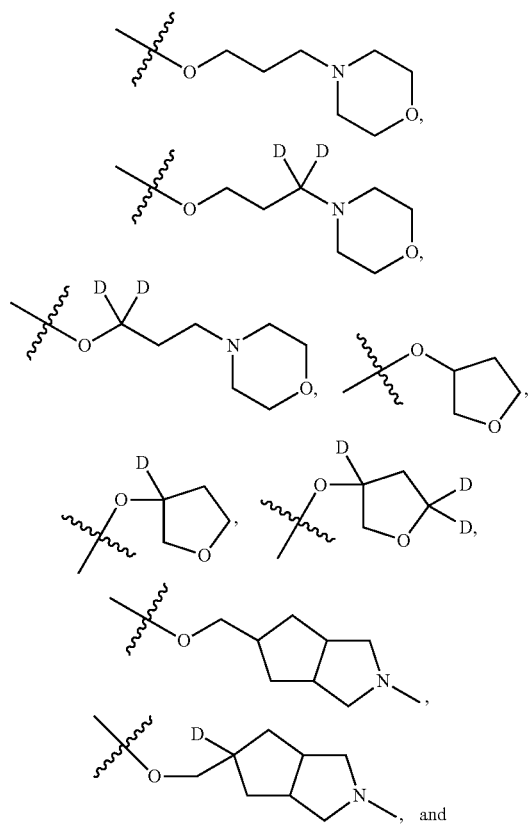

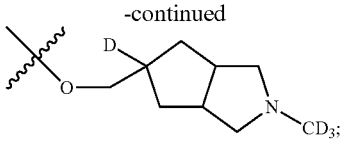

$R^x$, at each occurrence, is independently hydrogen or deuterium;

$R^e$ and $R^f$ are each independently hydrogen, deuterium, or $C_1$-$C_4$ alkyl optionally comprising one or more deuterium atoms;

$R^p$ and $R^q$ are each independently hydrogen or deuterium;

$R^y$ and $R^z$ are each independently hydrogen or detuerium;

L is $C_1$-$C_4$ alkylene optionally comprising one or more deuterium atoms;

$R^6$ is selected from hydrogen, deuterium, $C_1$-$C_4$ alkyl, aryl, heteroaryl, cycloalkyl, carbocyclyl, heterocyclyl, —$SR^{11}$, and —$OR^7$, wherein said alkyl, aryl, heteroaryl, cycloalkyl, carbocyclyl, and heterocyclyl each may optionally comprise one or more deuterium atoms;

$R^7$ is hydrogen, deuterium, $C_1$-$C_6$ alkyl, aryl, heteroaryl, cycloalkyl, carbocyclyl, heterocyclyl, or -$L^5$-$R^{20}$, wherein said alkyl, aryl, heteroaryl, cycloalkyl, carbocyclyl, and heterocyclyl each may optionally comprise one or more deuterium atoms;

$R^8$ is hydrogen, deuterium, $C_1$-$C_6$ alkyl, or benzyl, wherein said alkyl and benzyl each may optionally comprise one or more deuterium atoms;

$R^9$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{10}$ is hydrogen, deuterium, $C_1$-$C_6$ alkyl, $C_3$-$C_6$ cycloalkyl, aryl, or heteroaryl, wherein said alkyl, cycloalkyl, aryl, and heteroaryl each may optionally comprise one or more deuterium atoms;

$R^{11}$ is hydrogen, deuterium, $C_1$-$C_6$ alkyl, cycloalkyl, aryl, heteroaryl, or heterocyclyl, wherein said alkyl, cycloalkyl, aryl, heteroaryl, and heterocyclyl each may optionally comprise one or more deuterium atoms;

$R^{12}$ is $C_1$-$C_6$ alkyl, $C_3$-$C_6$ cycloalkyl, aryl, heteroaryl, or $NR^cR^d$, wherein said alkyl, cycloalkyl, aryl, and heteroaryl each may optionally comprise one or more deuterium atoms;

$R^{13}$ is $C_3$-$C_6$ cycloalkyl optionally substituted by one or more substituents independently selected from halogen, $C_1$-$C_6$ alkyl, $C_1$-$C_6$ alkoxy, oxo, or —$C(O)NR^cR^d$ and optionally comprising one or more deuterium atoms;

$L^5$ is methylene or ethylene, each optionally comprising one or more deuterium atoms;

$R^{20}$ is aryl or heteroaryl, each optionally comprising one or more deuterium atoms;

$R^a$ and $R^b$ are independently selected from hydrogen, deuterium, alkyl, alkenyl, alkynyl, aryl, heteroaryl, and benzyl, wherein said alkyl, alkenyl, alkynyl, aryl, heteroaryl, and benzyl each may optionally comprise one or more deuterium atoms;

$R^c$ and $R^d$ are each independently hydrogen, deuterium, $C_1$-$C_6$ alkyl, benzyl, or aryl wherein said alkyl, aryl, and benzyl each may optionally comprise one or more deuterium atoms; and wherein any said aryl, heteroaryl, and benzyl each may optionally be substituted with one to five substituents independently selected from $C_1$-$C_6$ alkyl, $C_1$-$C_4$ haloalkyl, $C_1$-$C_6$ alkoxy, $C_1$-$C_4$ haloalkoxy, halogen, hydroxyl, cyano, and nitro;

wherein any said carbocyclyl, cycloalkyl, or heterocyclyl may optionally be substituted with one or more substituents independently selected from $C_1$-$C_6$ alkyl, $C_1$-$C_4$ haloalkyl, $C_1$-$C_6$ alkoxy, halogen, hydroxyl, and oxo;

wherein each said alkyl, haloalkyl, alkoxy, haloalkoxy, and hydroxyl may optionally comprise one or more deuterium atoms; and wherein at least one of $R^1$, $R^2$, $R^3$, $R^4$, $R^5$, $R^x$, $R^e$, $R^f$, $R^p$, $R^q$, $R^y$, $R^z$, or Y comprises one or more deuterium atoms.

2. The compound of claim 1 or a pharmaceutically acceptable salt thereof, wherein Y is selected from hydrogen, deuterium,

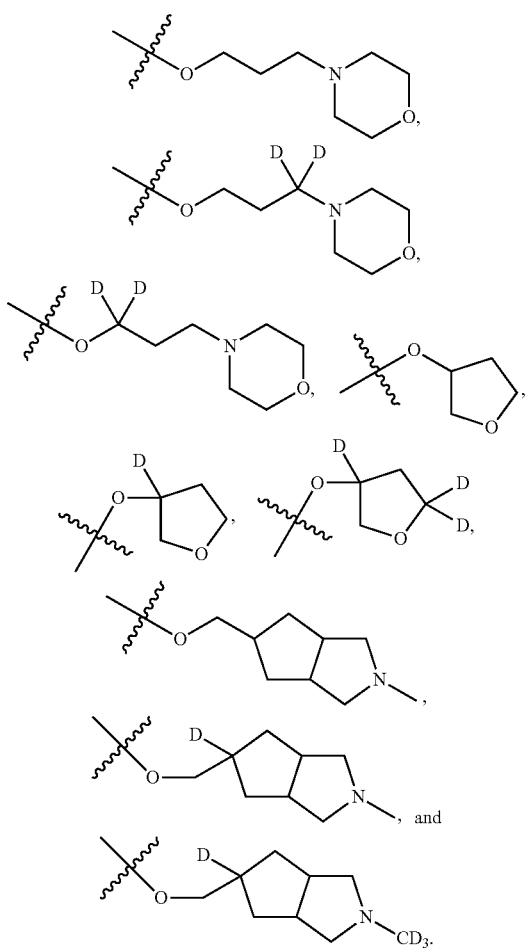

3. The compound of claim 2 or a pharmaceutically acceptable salt thereof, wherein Y is

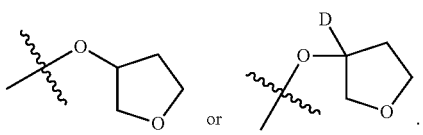 [SMILES: *OC1CCOC1 ; *OC1([2H])CCOC1]

4. The compound of claim 1 or a pharmaceutically acceptable salt thereof, wherein $R^e$ and $R^f$ are each independently $CH_3$ or $CD_3$.

5. The compound of claim 4 or a pharmaceutically acceptable salt thereof, wherein each of $R^e$ and $R^f$ is $CD_3$.

6. The compound of claim 1 or a pharmaceutically acceptable salt thereof, wherein $R^1$ is selected from hydrogen, deuterium, F, Cl,

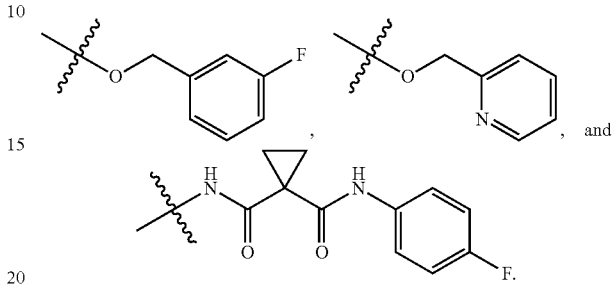

7. The compound of claim 6 or a pharmaceutically acceptable salt thereof, wherein $R^1$ is hydrogen or F.

8. The compound of claim 1 or a pharmaceutically acceptable salt thereof, wherein $R^2$ and $R^4$ are each independently selected from hydrogen, deuterium, F, Cl, —C≡CH, and —C≡CD.

9. The compound of claim 8 or a pharmaceutically acceptable salt thereof, wherein $R^2$ is Cl or —C≡CH and $R^4$ is hydrogen.

10. The compound of claim 1 or a pharmaceutically acceptable salt thereof, wherein $R^3$ and $R^5$ are each independently selected from hydrogen, deuterium, and F.

11. The compound of claim 10 or a pharmaceutically acceptable salt thereof, wherein each of $R^3$ and $R^5$ is hydrogen.

12. The compound of claim 1 or a pharmaceutically acceptable salt thereof, wherein each $R^x$ is hydrogen.

13. The compound of claim 1 or a pharmaceutically acceptable salt thereof, wherein $R^p$, $R^q$, $R^y$, and $R^z$ are each hydrogen.

14. The compound of claim 1 or a pharmaceutically acceptable salt thereof, wherein the compound is (S,E)-N-(4-(3-chloro-4-fluorophenylamino)-7-(tetrahydrofuran-3-yloxy)quinazolin-6-yl)-4-($D_6$-dimethylamino)but-2-enamide;

(S,E)-4-($D_6$-dimethylamino)-N-(4-(3-ethynylphenylamino)-7-(tetrahydro furan-3-yloxy)quinazolin-6-yl)but-2-enamide;

(E)-N-(4-(3-chloro-4-fluorophenylamino)-7-((3-D)-tetrahydrofuran-3-yloxy)quinazolin-6-yl)-4-(dimethylamino)but-2-enamide; or (E)-4-(dimethylamino)-N-(4-(3-ethynylphenylamino)-7-(3-D-tetrahydrofuran-3-yloxy)quinazolin-6-yl)but-2-enamide.

15. A composition comprising a compound of claim 1 or a pharmaceutically acceptable salt thereof and a pharmaceutically acceptable carrier.

16. The composition of claim 15, further comprising a second agent.

17. The composition of claim 16, wherein said second agent is a tyrosine kinase inhibitor.

\* \* \* \* \*

UNITED STATES PATENT AND TRADEMARK OFFICE
CERTIFICATE OF CORRECTION

Page 1 of 1

PATENT NO. : 8,735,409 B2
APPLICATION NO. : 13/513982
DATED : May 27, 2014
INVENTOR(S) : Qiang Zhang and Hongwen Zhu It is certified that error appears in the above-identified patent and that said Letters Patent is hereby corrected as shown below:

In the Claims:

Column 58, line 14

In claim 1, delete "detuerium" and insert -- deuterium --.

Column 60, line 47

In claim 14, delete "7-(tetrahydro furan" and insert -- 7-(tetrahydrofuran --.

Signed and Sealed this
Seventh Day of October, 2014

Michelle K. Lee
*Deputy Director of the United States Patent and Trademark Office*